US010463656B2

(12) United States Patent
Carlson et al.

(10) Patent No.: US 10,463,656 B2
(45) Date of Patent: Nov. 5, 2019

(54) METHODS AND COMPOSITIONS FOR PREVENTION OF FEEDLOT BOVINE RESPIRATORY DISEASE

(71) Applicant: Iowa State University Research Foundation, Inc., Ames, IA (US)

(72) Inventors: Steven Alan Carlson, Story City, IA (US); Timothy L. Day, Gilbert, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 33 days.

(21) Appl. No.: 15/863,226

(22) Filed: Jan. 5, 2018

(65) Prior Publication Data

US 2018/0185344 A1 Jul. 5, 2018

Related U.S. Application Data

(60) Provisional application No. 62/442,770, filed on Jan. 5, 2017.

(51) Int. Cl.
*A61K 31/444* (2006.01)
*A61K 31/395* (2006.01)
*A61K 31/546* (2006.01)
*C12Q 1/6883* (2018.01)

(52) U.S. Cl.
CPC .......... *A61K 31/444* (2013.01); *A61K 31/395* (2013.01); *A61K 31/546* (2013.01); *C12Q 1/6883* (2013.01); *C12Q 2600/158* (2013.01)

(58) Field of Classification Search
CPC ................................................. A61K 31/444
USPC ...................................................... 514/196
See application file for complete search history.

(56) References Cited

U.S. PATENT DOCUMENTS

| | | | |
|---|---|---|---|
| 5,407,941 A | 4/1995 | Carceller et al. | |
| 5,476,856 A * | 12/1995 | Carceller ............. | C07D 401/04 514/290 |
| 5,514,691 A | 5/1996 | Chan et al. | |
| 5,571,821 A | 11/1996 | Chan et al. | |
| 5,591,761 A | 1/1997 | Chan et al. | |
| 5,594,021 A | 1/1997 | Chan et al. | |
| 5,804,585 A | 9/1998 | Verner | |
| 5,958,905 A | 9/1999 | Chan et al. | |
| 5,962,490 A | 10/1999 | Chan et al. | |
| 5,977,117 A | 11/1999 | Chan et al. | |
| 6,013,655 A | 1/2000 | Verner | |
| 6,030,991 A | 2/2000 | Chan et al. | |
| 6,248,767 B1 | 6/2001 | Blok et al. | |
| 6,265,428 B1 | 7/2001 | Chan et al. | |
| 6,329,387 B2 | 12/2001 | Verner | |
| 6,331,637 B1 | 12/2001 | Chan et al. | |
| 6,342,610 B2 | 1/2002 | Chan et al. | |
| 6,384,261 B1 | 5/2002 | Chan et al. | |
| 6,420,567 B1 | 7/2002 | Wu et al. | |
| 6,432,994 B1 | 8/2002 | Wu et al. | |
| 6,458,805 B2 | 10/2002 | Blok et al. | |
| 6,545,014 B2 | 4/2003 | Verner | |
| 6,613,804 B2 | 9/2003 | Chan et al. | |
| 6,632,829 B2 | 10/2003 | Wu et al. | |
| 6,683,103 B2 | 1/2004 | Wu et al. | |
| 6,709,676 B2 | 3/2004 | Cho | |
| 6,803,468 B2 | 10/2004 | Kumar et al. | |
| 6,979,463 B2 | 12/2005 | Kou | |
| 7,405,223 B2 | 7/2008 | Affrime et al. | |
| 7,618,649 B2 | 11/2009 | Cho | |
| 7,820,199 B2 | 10/2010 | Kou | |
| 7,902,208 B2 | 3/2011 | Affrime et al. | |
| 8,034,845 B2 * | 10/2011 | Freehauf ............. | A61K 9/0019 514/618 |
| 8,129,169 B2 | 3/2012 | Van Dien et al. | |
| 8,187,630 B2 | 5/2012 | Cho | |
| 9,241,936 B2 | 1/2016 | Hu | |
| 9,434,964 B2 | 9/2016 | Van Dien et al. | |
| 2002/0150593 A1 | 10/2002 | Hymas et al. | |
| 2003/0077254 A1 | 4/2003 | Ramaekers | |
| 2003/0086971 A1 | 5/2003 | Kou | |
| 2003/0208084 A1 | 11/2003 | Wu et al. | |
| 2004/0044216 A1 | 3/2004 | Kumar et al. | |
| 2004/0156865 A1 | 8/2004 | Confer et al. | |
| 2006/0078572 A1 | 4/2006 | Confer et al. | |
| 2006/0159761 A1 | 7/2006 | Kou | |
| 2007/0036859 A1 | 2/2007 | Perry et al. | |
| 2008/0064713 A1 | 3/2008 | Toyoda et al. | |
| 2009/0197907 A1 | 8/2009 | Parthasaradhi Reddy et al. | |
| 2011/0045575 A1 | 2/2011 | Van Dien et al. | |
| 2012/0225463 A1 | 9/2012 | Van Dien et al. | |
| 2016/0355846 A1 | 12/2016 | Van Dien et al. | |

FOREIGN PATENT DOCUMENTS

| | | |
|---|---|---|
| CN | 2000137356 A | 12/2000 |
| CN | 2008105209 A | 1/2008 |
| WO | 2006103688 A1 | 10/2006 |
| WO | 2006114676 A2 | 11/2006 |
| WO | 2006114676 A3 | 11/2006 |
| WO | 2010141920 A2 | 12/2010 |
| WO | 2010141920 A3 | 12/2010 |

OTHER PUBLICATIONS

McClenahan [online] (Neutrophils activation and lung injury in bovine pneumonic pasteurellos (Jun. 2001, pp. 1-173) Retrieved on Nov. 8, 2018 (Year: 2001).*
Merlos et al. (Journal of Pharmacology and Experimental Therapeutics (1997), vol. 280, pp. 114-121). (Year: 1997).*
Cellai et al. (FASEB Journal (2002), vol. 16, pp. 733-735) (Year: 2002).*
Maiti, Ritupama et al., "Rupatadine and Levocetirizine for Seasonal Allergic Rhinitis", Arch Otolaryngol Head Neck Surg., vol. 136, (No. 8), pp. 796-800. Aug. 2010.

(Continued)

*Primary Examiner* — Melenie L Gordon
*Assistant Examiner* — Taina D Matos Negron
(74) *Attorney, Agent, or Firm* — McKee, Voorhees & Sease, PLC

(57) ABSTRACT

Methods for preventing feedlot bovine respiratory diseases employing an anti-inflammatory drug rupatadine are disclosed. Compositions are further disclosed. Beneficially, the methods and compositions provide safe and cost-effective management of a costly disease.

17 Claims, 23 Drawing Sheets

Specification includes a Sequence Listing.

(56) References Cited

OTHER PUBLICATIONS

Mullol, J. et al., "Update on Rupatadine in the Management of Allergic Disorders", European Journal of Allergy and Clinical Immunology, Allergy 2015; 70: pp. 1-24.
Fulton, Robert W. et al., "Lung Pathology and Infectious Agents in Fatal Feedlot Pneumonias and Relationship with Mortality, Diease Onset, and Treatments", J Vet Diagn Invest., 21: pp. 464-477. 2009.
Cernicchiaro, N. et al., "Associations Between the Distance Traveled from Sale Barns to Commercial Feedlots in the United States and Overall Performance, Risk of Respiratory Disease, and Cumulative Mortality in Feeder Cattle During 1997 to 2009", American Society of Animal Science, pp. 1929-1939. Jan. 20, 2015.
Cernicchiaro, N. et al., "Associations Between Weather Conditions During the First 45 Days After Feedlot Arrival and Daily Respiratory Disease Risks in Autumn-Placed Feeder Cattle in the United States", American Society of Animal Science, pp. 1328-1337. Jan. 20, 2015.
Babcock, A. H. et al., "Feedlot Health and Performance Effects Associated with the Timing of Respiratory Disease Treatment", American Society of Animal Science, pp. 314-327. Dec. 5, 2014.
Miles, Delbert G., Overview of the North American Beef Cattle Industry and the Incidence of Bovine Respiratory Disease (BRD), Animal Health Research Reviews 10(2); pp. 101-103. Oct. 23, 2009.
Czuprynski, Charles J., "Host Response to Bovine Respiratory Pathogens", Animal Health Research Reviews 10 (2); pp. 141-143. Oct. 15, 2009.
Taylor, Jared D. et al., "The Epidemiology of Bovine Respiratory Disease: What is the Evidence for Preventive Measures?", Can Vet J, vol. 51, pp. 1351-1359. Dec. 2010.
Munoz-Cano, Rosa et al., "Evaluation of Nasal Symptoms Induced by Platelet Activating Factor, After Nasal Challenge in Both Healthy and Allergic Rhinitis Subjects Pretreated with Rupatadine, Levocetirizine or Placebo in a Cross-Over Study Design", Allergy, Asthma & Clinical Immunology, 9: 43, pp. 1-5. 2013.
Francoz, David et al., "Evidence Related to the Use of Ancillary Drugs in Bovine Respiratory Disease (Anti-Inflammatory and Others): Are the Justified or Not?", Vet Clin. Food Animal pp. 23-38. 2012.
Griffin, Dee et al., "Bacterial Pathogens of the Bovine Respiratory Disease Complex", Vet Clin. Food Animal, pp. 381-394. 2010.
United States Department of Agriculture, "Types and Costs of Respiratory Disease Treatments in U.S. Feedlots", Animal and Plant Health Inspection Service, pp. 1-2. Apr. 2013.
Munoz-Cano, R. et al, Abstract Only No. 465, Effects of Rupatadine on Platelet Activating Factor (PAF)-induced Human Mast Cell Degranulation Compared With Desloratadine and Levocetirizine, J Allergy Clin Immunol Feb. 2012.

\* cited by examiner

```
Identities              Positives              Gaps

289/341(85%)            311/341(91%)           0/341(0%)

Query   1    MEPHDSSHMDSEPRYTLFPIVYSIIFVLGVIANGYVLWVFARLYPCKKFNEIKIFMVNLT   60
             MEP++S  +DSEPRYTLFPI YSI+FVLGVIAN YVLWVFARLYP KRFNEIKIFMVNLT
Sbjct  11    MEPNNSFRVDSEPRYTLFPIFYSIVFVLGVIANSYVLWVFARLYPSKRFNEIKIFMVNLT   70

Query   61   MADMLFLITLPLWIVYYQNQGNWILPKFLCNVAGCLFFINTYCSVAFLGVITYNRFQAVT   120
             MAD+LFL+TLPLWIVYY NQG+WILPKFLCN+AGC FFINTYCSVAFL VITYNRFQAVT
Sbjct  71    MADLLFLVTLPLWIVYYYNQGDWILPKFLCNLAGCFFFINTYCSVAFLAVITYNRFQAVT   130

Query  121   RPIKTAQANTRKRGISLSLVIWVAIVGAASYFLILDSTNTVPDSAGSGNVTRCFEHYEKG   180
             RPIKTAQA TRKRGI LSL+IWV+IVGAASYF +LDSTN  P+  GS N+TRCFEHYEKG
Sbjct  131   RPIKTAQATTRKRGILLSLIIWVSIVGAASYFFVLDSTNREPNKTGSANITRCFEHYEKG   190

Query  181   SVPVLIHIFIVFSFFLVFLIILFCNLVIIRTLLMPVQQQRNAEVKRRALWMVCTVLAV    240
             S+PVL IHIF+VFSFFLVFLIILFCNLVIIRTLL Q VQ QRNAEVKRRALWMVCTVLAV
Sbjct  191   SIPVLTIHIFLVFSFFLVFLIILFCNLVIIRTLLTQQVQIQRNAEVKRRALWMVCTVLAV   250

Query  241   FIICFVPHHVVQLPWTLAELGFQDSKFHQAINDAHQVTLCLLSTNCVLDPVIYCFLTKKF   300
             FIICFVPHH+VQLPWTLAELGFQD+ FHQAINDAHQVTLCLLSTNCVLDP+IYCFLTKKF
Sbjct  251   FIICFVPHHLVQLPWTLAELGFQDTDFHQAINDAHQVTLCLLSTNCVLDPIIYCFLTKKF   310

Query  301   RKHLTEKFYSMRSSRKCSRATTDTVTEVVPFNQIPGNSLK  341  (SEQ. I.D. NO 3)
             RKHLTEK YSMR SRKCSRAT++T TEVV+   +P SLK
Sbjct  311   RKHLTEKLYSMRESRKCSRATSETGTEVVMQLKDVPVKSLK 351  (SEQ. I.D. NO 2)
```

*FIG. 24*

METHODS AND COMPOSITIONS FOR PREVENTION OF FEEDLOT BOVINE RESPIRATORY DISEASE

CROSS-REFERENCE TO RELATED APPLICATIONS

This application claims priority to provisional application U.S. Ser. No. 62/442,770 filed Jan. 5, 2017, which is incorporated herein by reference in its entirety.

FIELD OF THE INVENTION

The present invention is related to compositions and methods for preventing feedlot bovine respiratory diseases employing an anti-inflammatory drug rupatadine. Compositions comprising rupatadine provide safe and cost effective BRD prevention.

BACKGROUND OF THE INVENTION

Bovine Respiratory Disease (BRD), a respiratory distress syndrome, is the leading cause of death in U.S. beef cattle and also the costliest disease of domestic beef cattle. BRD requires expensive treatment (estimated at least $151.18 per animal, or about $500 million per year in the U.S.) and compromises the growth of affected animals. The disease results in lost production and medical expenditures with the most recent comprehensive U.S. Department of Agriculture data published in 2013 revealing that the incidence of the disease is about 16%. Overall, the disease is estimated to cost more than $1 billion dollars in total cost per year in the U.S.

BRD is known to involve numerous bovine respiratory viruses. For example, herpesvirus-1, bovine respiratory syncytial virus, parainfluenzavirus-3, bovine coronavirus, bovine viral diarrhea virus, bovine reovirus, *Mannheimia haemolytica*, *Pasteurella multocida*, *Histophulus somni*, and *Mycoplasma bovis* have all been implicated in BRD. Vaccines are not currently effective for prevention of such viral respiratory diseases, including BRD. In addition, various bacterial pathogens are associated with BRD. Given the complex bacterial and viral etiologies involved with BRD, prevention and treatment of this disease complex is difficult. Current production management practices used by the industry only alleviate part of the problem. For example, available vaccines do not target all of the BRD-causing pathogens, and antibiotic metaphylaxis does not eliminate all BRD-causing respiratory bacteria. Moreover, the recent approval of two new BRD-targeted antibiotics (gamithromycin and tildipirosin) suggests that the currently available drugs are inadequate despite advances in antimicrobial therapy, as BRD continues to plague the cattle industry. There are also no effective broad prevention strategies currently available.

Susceptibility to BRD has been suggested in some cattle breeds, but other studies indicate that BRD susceptibility lacks a heritable genetic basis. Given the uncertainty of genotypes that determine BRD resistance or susceptibility and the overuse of metaphylactic antibiotics used versus BRD, a non-antibiotic solution is a desirable approach and an objective of the present invention. Antibiotic-independent prevention of BRD would beneficially reduce the prevalence of this costly disease, and prevention would reduce disease-associated costs and the overuse of metaphylactic antibiotics that contributes to antibiotic resistance. Because BRD remains the single most expensive and deadly beef cattle disease in the U.S., development of new technologies and approaches that effectively reduce BRD incidence is critical to promote both animal health and animal production.

The inflammatory process elicited, directly or indirectly, by BRD involved microbes is an under-appreciated component of BRD. The significant inflammatory components include neutrophil attraction and adherence, leukocytolysis, increased vascular permeability at the level of the endothelium, and pro-coagulation. These components have many potential factors, some characterized and some uncharacterized. Anti-inflammatory drugs have not been fully explored for metaphylaxis or prophylaxis of BRD. Therefore, the inflammatory component of BRD is a highly meritorious and logical point for novel interventions.

Accordingly, it is an objective of the invention to provide compositions for preventing feedlot bovine respiratory diseases employing the anti-inflammatory drug rupatadine. It is also an objective of the invention to provide a method for utilizing the compositions. It is also an objective of the invention to provide assays for detecting a population of cattle in need of treatment or prevention of the bovine respiratory disease, including kits for the same.

Other objects, advantages and features of the present invention will become apparent from the following specification taken in conjunction with the accompanying examples or drawings.

BRIEF SUMMARY OF THE INVENTION

In one embodiment anti-inflammatory compositions, including rupatadine, for prevention of BRD in a feedlot are provided.

In another embodiment, methods of preventing BRD in a feedlot employing the anti-inflammatory compositions are provided.

Additional aspects include kits for excess PAFR in a cattle population, comprising: a PAFR capture reagent, including one or more of a PAFR-specific oligonucleotide and/or a labeled probe; and a PAFR-specific antibody, which may be labeled, and/or a labeled antibody specific to the PAFR-specific antibody; and optionally instructions for use.

Further embodiments include kits for inducing and assaying PAFR in a cattle population, the kits further comprising reagents to induce expression of PAFR in a sample.

Certain embodiments include methods for detecting PAFR in a sample, comprising: capturing a PFAR RNA, cDNA, and/or a protein in the sample; and assaying the quantity of PAFR RNA, cDNA, and/or protein in the sample.

Yet further embodiments include kits for detecting PAFR using PCR, comprising: a forward primer specific for said PAFR; a reverse primer specific for said PAFR; PCR reagents; and instructions for use.

Other embodiments include systems for detecting PAFR using PCR, comprising: a sample; a forward primer specific for said PAFR; a reverse primer specific for said PAFR; PCR reagents; a way to detect the PCR product; and instructions for use.

Further embodiments include a system for detecting PAFR using labeled oligonucleotide probes, the system further comprising a labeled oligonucleotide probe specific for said PAFR.

Additional embodiments include a system for detecting PAFR using labeled antibodies, comprising: a sample; an antibody that binds to said PAFR, which may be labeled; protein binding reagents; a way to detect the bound PAFR; and instructions for use.

Further embodiments include a system with a secondary antibody specific to the PAFR-specific antibody, which may be labeled.

Additional embodiments comprise a kit for detecting the presence of a PAFR protein or peptide, comprising: a substrate having a capture agent for said PAFR protein or peptide; an antibody specific for said PAFR protein or peptide; a reagent capable of labeling bound antibody for said PAFR protein or peptide; and instructions for use.

Other embodiments are methods for detecting bovine which are BRD sensitive, comprising: taking a sample from said bovine; treating the sample to induce PAFR expression; and using a kit or system to assay PAFR expression.

A major benefit of the current invention over the prior art is the establishment of the ex vivo and in vivo confirmed direct link between a respiratory mediator, platelet activating factor (PAFR) and a pro-inflammatory response in the lungs that contributes to BRD. Beneficially the compositions according to the invention prevent and treat BRD in beef cattle through the anti-inflammatory effects of the compositions comprising rupatadine.

The foregoing summary is illustrative only and is not intended to be in any way limiting. In addition to the illustrative aspects, embodiments, and features described above, further aspects, embodiments, and features will become apparent by reference to the drawings and the following detailed description. Accordingly, the drawings and detailed description are to be regarded as illustrative in nature and not restrictive.

BRIEF DESCRIPTION OF THE DRAWINGS

FIG. 24 shows the alignment of a bovine PAFR protein (Sbjct, SEQ ID NO: 2) to the human PAFR protein (Query, SEQ ID NO: 3).

Figure 1:
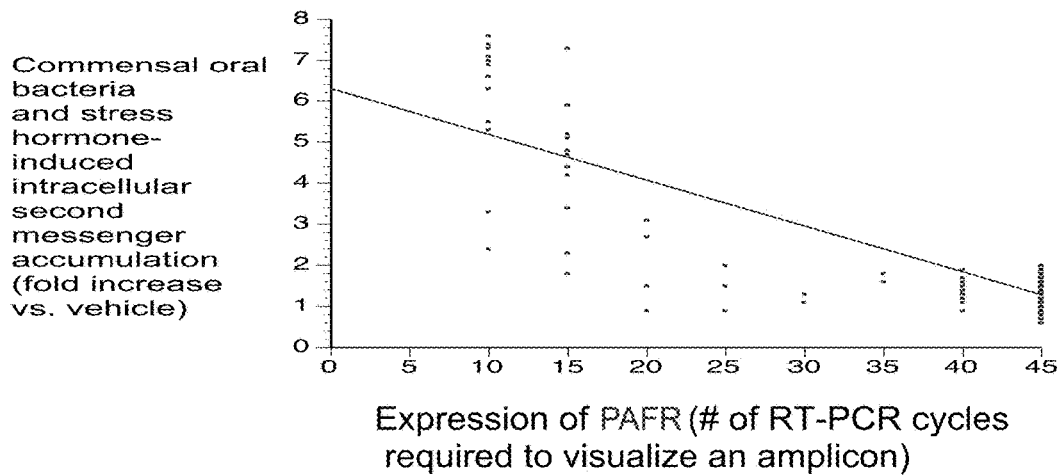
FIG. 1 shows PAFR expression in relation to a second messenger accumulation in individual bovine blood samples incubated with commensal oral bacteria and stress hormones as detailed in Example 1.

Various embodiments are described in detail with reference to the drawings, wherein like reference numerals represent like parts throughout the several views. Reference to various embodiments does not limit the scope of the invention. Figures represented herein are not limitations to the various embodiments according to the invention and presented for exemplary illustration of the invention.

DETAILED DESCRIPTION OF THE PREFERRED EMBODIMENT

The present invention relates to preventative compositions and methods of employing the same for BRD. The embodiments of this invention are not limited to those methods and compositions disclosed herein, which can vary and are understood by skilled artisans based on the disclosure herein of the present invention. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and moreover may modify the typical measurements referenced herein, and the like. Whether or not modified by the term "about", the claims include equivalents to the quantities.

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and Fab$_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence.

The term "bovine", as used herein, means a diverse group of medium- to large-sized ungulates, generally having cloven hoofs, and at least one of the sexes having true horns. Bovines include, but are not limited to, domestic cattle.

The terms "diagnose", "diagnosing" or "diagnostic", as used herein, mean the identification of the nature and/or cause of something, such as a disease, or a kit which is useful for making such identification.

The term "BRD sensitive" refers to an animal that has an increased expression in PAFR RNA when compared to the rest of the herd and/or protein in response to stress, such as but not limited to stress related to transporting the animal from one location to another; drugs which simulate this response, such as but not limited to cortisol, adrenalin, and/or norepinephrine; and/or to a bacterial challenge, such as but not limited to infection, bacterial lysate, bacterial components, and/or static bacteria.

The term "housekeeping gene" refers to a gene that does not alter its expression due to a change in certain environments or to certain stimuli. They are typically, but not always, constitutive genes that have a function in basic cellular function, and are expressed in all cells under normal and pathophysiological conditions.

The term "kit" as used herein refers to a set of reagents for the purpose of performing the method of the invention, more particularly, the identification of PAFR expression in cattle.

The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (e.g. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications such as (a) an alternative linking group, (b) an analogous form of purine, (c) an analogous form of pyrimidine, or (d) an analogous sugar. For examples of analogous linking groups, purine, pyrimidines, and sugars see for example, WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylguanosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylguanosine, 5'-methoxycarboxymethyluracil, 5-methoxyuracil, 2-methylthio-N6-isopentenyladenine, uracil-5-oxyacetic acid (v) ybutoxosine, pseudouracil, guanosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N2-carboxypropyl)uracil, and 2,6-diaminopurine. The polynucleotide sequences herein may be prepared by any known method, including synthetic, recombinant, ex vivo generation, or a combination thereof, as well as utilizing any purification methods known in the art. Methylenemethylimino linked oligonucleotides as well as mixed backbone compounds, may be prepared as described in U.S. Pat. Nos. 5,378,825; 5,386,023; 5,489,677; 5,602,240; and 5,610,289. Formacetal and thioformacetal linked oligonucleotides may be prepared as described in U.S. Pat. Nos. 5,264,562 and 5,264,564. Ethylene oxide linked oligonucleotides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. No. 5,610,289 or 5,625,050. Phosphoramidite oligonucleotides may be prepared as described in U.S. Pat. No. 5,256,775 or 5,366,878. Alkylphosphonothioate oligonucleotides may be prepared as described in WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198.

As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified).

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers;

thus, peptides, oligopeptides, and proteins are included within the definition of polypeptide.

The term "pharmaceutical agent" or "drug" refers to a chemical compound or composition capable of inducing a desired therapeutic or prophylactic effect when properly administered to a subject.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The term "prevent," "prevention," "metaphylaxis" or "prophylaxis" as referred to herein means the disease (BRD) does not occur in an animal which may be predisposed to the disease or under conditions in which the disease prevalence is high, or that the disease is inhibited, frequency and/or severity is reduced.

The term "therapeutically effective amount" (or "effective amount") refers to an amount of an active ingredient, e.g., a therapeutic agent according to the invention, sufficient to effect beneficial or desired results when administered to a subject. An effective amount can be administered in one or more administrations, applications or dosages. A therapeutically effective amount of a composition according to the invention may be readily determined by one of ordinary skill in the art.

The term "sample" as referred to herein means an isolated part of an animal. Samples can include, but are not limited to, drawn blood, lung lavage, and tissue biopsies.

The term "veterinarily-acceptable carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Embodiments of the Invention

According to an embodiment of the invention, methods and compositions for preventing BRD, kits for detection of PAFR in samples from cattle, and systems to inducing expression and assaying PAFR are provided. The methods and compositions overcome shortcomings of the conventional vaccine technologies and/or antimicrobial therapies commercially available which are insufficient in preventing BRD, which continues to plague the cattle industry. As no broadly effective strategy to combat this disease is currently available, the present invention provides a safe and cost effective anti-BRD drug to reduce this problem and its associated costs. The embodiments of the present invention provide use of a human-approved anti-PAFR drug (or PAFRi/PAFR antagonist) as an effective prophylactic agent against BRD. Beneficially, the prophylaxis or metaphylaxis of BRD with the anti-PAFR therapeutic agent according to the invention will decrease reliance and use of antibiotics as conventionally are administered to most animals. In an embodiment, the methods of the invention result in at least a 50% reduction in antibiotic usage within a facility, or at least a 55% reduction in antibiotic usage within a facility, or at least a 60% reduction in antibiotic usage within a facility, or greater. As a further benefit, the reduced usage of unnecessary antibiotics further results in a decrease in antibiotic resistance.

In a further embodiment, the methods result in being able to identify BRD sensitive cattle with a false negative rate of less than about 10%, or with a false negative rate of less than about 9%, or with a false negative rate of less than about 8%, or with a false negative rate of less than about 7%, or with a false negative rate of less than about 6%, or with a false negative rate of less than about 5%, or with a false negative rate of less than about 4%, or with a false negative rate of less than about 3%, or with a false negative rate of less than about 2%, or with a false negative rate of less than about 1%, or with a false negative rate at about 0%.

One of ordinary skill in the art can easily calculate the false negative rate using statistics common to the assay used. As a non-limiting aspect, for the calculation of the false negative rate for quantitative PCR, one skilled in the art could calculate the copy number of PAFR transcripts per a quantity of total RNA and compare this amount to the copy number of transcripts of a housekeeping gene, such as, but not limited to, UBC. These ratios could be then compared to which cattle develop BRD after being stressed and a cutoff threshold could then be calculated for that ratio of PAFR and housekeeping genes. For example, a cutoff value in the range of PAFR to UBC ratio of about 2 to about 10 transcripts per 200 ng total RNA provides a low false positive rate, or more preferably a ratio between about 2 and about 7 transcripts per 200 ng total RNA, or even more preferably a ratio above 2 transcripts per 200 ng total RNA.

Compositions

The compositions according to the invention include an anti-inflammatory agent that is efficacious against PAFR. This therapeutic agent or drug may also be designated as PAFRi or a PAFR inhibitor.

The compositions according to the invention include the antihistamine rupatadine, or its pharmaceutically acceptable derivatives, including salts, solvates or esters thereof. Rupatadine (8-chloro-11-[1-[(5-methyl-3-pyridyl)methyl]-4-piperidyliden]-6,11-dihydro-5H-benzo[5,6]cyclohepta[1,2-b]pyridine), CAS number 158876-82-5 has a molecular formula as $C_{26}H_{26}ClN_3$, molecular weight as 415.958, and the following structure:

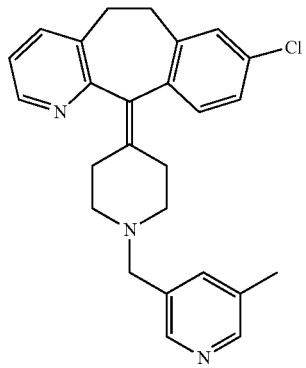 [SMILES: Cc1cncc(CN2CCC(=C3c4ccc(Cl)cc4CCc4cccnc43)CC2)c1]

Rupatadine is a second-generation antihistamine and platelet-activating factor (PAF) or platelet-activating factor receptor (PAFR) antagonist used to treat allergies in humans. The anti-histamine antagonist has selective peripheral H1 receptor antagonist activity and it further blocks the receptors of the platelet-activating factor (PAF) according to in vitro and in vivo studies thereby reducing proinflammaory properties. Rupatadine has several active metabolites such as desloratadine, 3-hydroxydesloratadine, 6-hydroxydesloratadine and 5-hydroxydesloratadine. Additional disclosure on the structure, pharmaceutically acceptable derivatives, formulations, and activity of rupatadine is disclosed, for example, in U.S. Pat. Nos. 5,407,941, 5,476,856, and 9,241,936, which are herein incorporated by reference in its entirety.

It is to be understood that the compositions referred to herein according to the invention may include rupatadine itself or any pharmaceutically acceptable derivatives, which also include its prodrugs which metabolize to the compound and the analogues and biologically active salt forms thereof, as well as optical isomers which provide the same pharmaceutical results.

Dosage Forms

Suitable forms for administration of the anti-inflammatory agent (also referred to as the therapeutic agent) that is efficacious against PAFR can be prepared for administration in the form of, for example, liquids, powders, aerosols, tablets, capsules, enteric-coated tablets or capsules, or suppositories. The compositions may also include, for example, suspensions, solutions, emulsions in oily or aqueous vehicles, pastes, and implantable sustained-release or biodegradable formulations. In an aspect, compositions include for example, tablets, powder, capsules, solutions (aqueous or non-aqueous), suspensions, syrups, emulsions or inhalable powders or aerosols. In preferred aspects of the invention, the composition is orally-administered to an animal and therefore the preferred forms for administration include tablets and/or capsules which are dissolved in a solution or solvent, or provided in a solution (aqueous or non-aqueous), syrup, suspensions or emulsion. Such orally-administered dosage forms are preferably food-grade and able to dosed or provided to an animal or subject with its feed. As the form of the composition may vary a skilled artisan will appreciate the content of the pharmaceutically effective compound will also vary, such as in the range of about 0.1 wt-% to about 90 wt-%, or between about 0.5 wt-% to about 50 wt-% of the oral composition. Such amounts are sufficient to achieve the dosage range specified hereinafter in the methods of the invention.

It is particularly preferable if the composition is administered orally. Suitable oral formulations may be provided in the form of tablets. Further suitable oral formulations may be obtained, for example, by mixing a solid composition (such as a tablet containing the therapeutic agent) with known solvents or diluents such as water or sweetened water. Syrups containing the therapeutic agent according to the invention may additionally contain a sweetener such as saccharine, cyclamate, glycerol or sugar and a flavor enhancer, e.g. a flavoring extract. They may also contain suspension adjuvants or thickeners such as sodium carboxymethyl cellulose, wetting agents such as, for example, condensation products of fatty alcohols with ethylene oxide, or preservatives such as p-hydroxybenzoates as a known in the art of pharmaceutical formulations and compounding.

In other aspects, the composition is administered by injection. The compositions can be made in the form of sterile aqueous solutions or dispersions suitable for injectable use, or made in lyophilized forms using freeze-drying techniques. Such compositions can be made in the form of suspensions or emulsions. In an exemplary embodiment of a formulation for injectable administration, the therapeutic agent is provided in dry (i.e., powder or granular) form for reconstitution with a suitable vehicle (e.g., sterile water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials, such as an emulsion, an ion exchange resin, a sparingly soluble polymer, or a sparingly soluble salt. In an embodiment of the compositions for delivery via injection, the compositions can include a veterinarily-acceptable carrier in a volume of between about 0.1 ml and about 10 ml. In another embodiment the volume of the carrier is between about 0.5 ml and about 5 ml.

The composition preparations of the present invention are manufactured in a manner which is itself well known in the art. For example, the pharmaceutical preparations may be made by means of conventional mixing, granulating, dissolving, lyophilizing processes. The processes to be used will depend ultimately on the physical properties of the active ingredient used.

Co-Formulations

The compositions of the invention can be further co-formulated with an antibiotic and/or vaccine and/or any veterinarily-acceptable carriers and/or adjuvants as conventionally utilized in the prevention of BRD.

Various antibiotics which may be suitable for co-formulation include for example: Tulathromycin, Penicillin, Penicillin (Procaine/Benzathine), Oxytetracycline, Enrofloxacin, Erythromycin, Tylosin, Sulfadimethoxine, Amoxicillin, Ampicillin, Ceftoifur, Tilmicosin and Florfenicol. More generally, antibiotics may include, but are not limited to, those from the classes of aminoglycosides, carbapenems, cephalosporins, glycopeptides, macrolides, penicillins, polypeptides, quinolones, sulfonamides, and tetracyclines.

Commercially available vaccines may further be combined with the compositions of the invention. In an embodiment, exemplary vaccines that can be combined with the compositions disclosed herein include those for prevention of infections due to *Mannheimia* spp.

Veterinarily-acceptable carriers and/or adjuvants, include for example, any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan. The composition may include other pharmaceutically-acceptable excipients for developing powder, liquid or suspension dosage forms, such as disclosed in Remington: The Science and Practice of Pharmacy, Vol. 2, 19th edition (1995), which is hereby incorporated by reference. The amounts and concentrations of carriers, adjuvants and/or additives useful in the compositions of the present invention can readily be determined by the skilled artisan.

Methods of Preventing BRD

The compositions and methods of the invention prevent BRD. In some embodiments, the prevention of BRD is most effective at the time of greatest susceptibility of the animal, i.e., during the first four weeks, first five weeks, or first six weeks following arrival at a feedlot form a cow-calf site. In a preferred embodiment, the compositions and methods of the invention prevent BRD during the first six weeks following arrival at a feedlot. This period may be referred to herein as the "stress period" or "period of stress" and refer to the period of time when the respiratory disease occurs most often in the animal.

In an aspect, the methods of the invention focus on treatment of cattle demonstrating signs of BRD, or at risk for developing BRD, including elevated body temperature (e.g.>102.6° C.), respiratory signs (e.g. nasal discharge, cough, dyspnea, tachypnea), decreased appetite, depression or combinations thereof.

In an aspect, the methods of preventing BRD include administering the compositions of the invention to an animal expressing the drug-susceptible biomarker associated with BRD susceptibility (PAFR). In an aspect, the methods of administering including providing the compositions to the animal expressing the BRD susceptible biomarker pro-inflammatory lung protein (PAFR). Without being limited to a particular mechanism of action or theory of the invention, for some cattle, commensal oral bacteria translocate to the respiratory tract and activate PAFR in the presence of stress hormones (such as norepinephrine and cortisol) that are frequently elevated in the systemic circulation during stressful events, such as transportation. In an aspect, the methods of the invention focus on pro-inflammatory responses in the lungs of cattle expressing or hyper expressing PAFR.

The methods may further comprise the initial step of assaying for PAFR expression in excess (e.g. 50% more messenger RNA when compared to a population of cattle, such as a population of cattle transported and/or undergoing stress-provoking conditions) in a population of cattle. Expression can be assayed using an array of tissues including, but not limited to, blood, such as disclosed herein.

In an aspect, the methods of preventing BRD include administering the compositions of the invention to an animal in need of such prophylaxis. The administering can be in any suitable forms for oral and/or inhaled consumption including for example, tablets, powder, capsules, solutions (aqueous or non-aqueous), suspensions, syrups, emulsions or inhalable powders or aerosols. In some aspects, the composition is administered to the mouth of the animal. In some aspects, the composition is administered into the feed of the animal which is thereafter consumed by the animal.

In other aspects, the methods of preventing BRD include administering the compositions of the invention to an animal in need of such prophylaxis by an injectable form. The administering can be in any suitable forms to be administered directly into the bloodstream, into muscle, or into an internal organ. Suitable means for parenteral administration include intravenous, intra-arterial, intraperitoneal, intrathecal, intraventricular, intraurethral, intrasternal, intracranial, intramuscular and subcutaneous. Suitable devices for parenteral administration include, for example, needles or microneedles. Parenteral formulations are typically aqueous solutions which can contain excipients and buffering agents (preferably to a pH of from about 3 to about 9, or from about 4 to about 8, or from about 5 to about 7.5, or from about 6 to about 7.5, or about 7 to about 7.5), but for some applications, they can be more suitably formulated as a sterile non-aqueous solution, or as a dried form to be used in conjunction with a suitable vehicle such as sterile water. The preparation of parenteral formulations under sterile conditions, for example, by lyophilisation, can readily be accomplished using standard pharmaceutical techniques well known to those skilled in the art.

In an aspect, the therapeutic agent is administered in a dose of between about 0.1-10 mg/kg/day, or between about 0.1-5 mg/kg/day, or between about 0.5-5 mg/kg/day. In another aspect, the therapeutic agent is administered in a dose of between about 0.1-1 mg/kg/day, or between about 0.3-1 mg/kg/day, or between about 0.5-1 mg/kg/day.

In an aspect, the therapeutic agent is administered in a dose of between about 0.1-20 mg/kg/week, or between about 0.1-10 mg/kg/week, or between about 0.5-10 mg/kg/week. In such an embodiment, weekly injections, such as weekly subcutaneous injections may be provided to an animal in need.

In an aspect, the therapeutic agent is administered in a dose of between about 1 mg to 100 mg, between about 10 mg to 100 mg, between about 30 mg to 100 mg, or between about 50 mg to 100 mg. In a preferred aspect the dosage is provided on a once a day basis for ease in administration.

In other aspects, it may be preferable to administer a single dose to animals, or, alternatively, two or more injections at a preferred interval. Formulations for parenteral administration can be formulated to be immediate and/or modified release. Extended or controlled release formulations can also be referred to as a long-acting injectable. Modified release formulations include delayed, sustained, pulsed, controlled, targeted and programmed release. The therapeutic agents of the invention can be formulated as a solid, semi-solid, or thixotropic liquid for administration as an implanted depot, providing modified release of the active compound. Examples of such formulations include drug-coated stents and poly(dl-lactic-coglycolic) acid (PLGA) microspheres. Those skilled in the art can readily determine the optimal administration regimen.

In an aspect, the methods of preventing BRD include inhibiting PAFR. The inhibition of PAFR and prevention of BRD is measured by clinical signs of BRD such as rhinorrhea, ocular discharge, coughing, dyspnea, anorexia, listlessness, etc. Physical examination of the animals with BRD may exhibit aberrant lung sounds (measured with the stethoscope or the WHISPER device) in combination with the other upper respiratory signs (e.g., rhinorrhea or ocular discharge) plus pyrexia (rectal temperature>102.6° F.) or listlessness or anorexia. According to the methods of prevention according to the invention, the BRD incidence is significantly lower in the pen of calves receiving the therapeutic agent when compared to the pen receiving a control (or conventional antibiotic and/or vaccine).

The methods of prevention may further include co-administering antibiotics and vaccines to the animal (or population of animals) that are determined to express or hyper express PAFR. Unlike conventional methods of preventing BRD, only those animals (estimated 10% incidence) predicted to develop BRD based on the expression or hyper expression of PAFR are treated with the antibiotic and/or vaccine. Beneficially, this significantly reduces the unnecessary usage of such treatments and the cost of employing the novel approach of BRD prevention (when factoring in the cost of antibiotics, vaccines, and production/death loses).

According to the invention, the methods of prevention provide at least a 50% reduction in BRD prevalence in treated animals, at least a 60% reduction in BRD prevalence in treated animals, at least a 70% reduction in BRD prevalence in treated animals, at least an 80% reduction in BRD prevalence in treated animals, or at least a 90% reduction in BRD prevalence in treated animals.

In an aspect, the therapeutic agent is absent from muscle tissues of the treated animal at three to six weeks post-withdrawal of the drug.

Assays

In the present invention, a sample of genetic material and/or protein is obtained from an animal. Samples can be obtained from blood, tissue, semen, etc. Generally, peripheral blood is used as the source, and the genetic material is RNA. A sufficient amount of cells are obtained to provide a sufficient amount for analysis. This amount will be known or readily determinable by those skilled in the art. The RNA and or protein is isolated from the sample by techniques known to those skilled in the art.

The term "semiquantitative PCR" refers to a kind of polymerase chain reaction (PCR), which can be carried out on tissue samples, on serum and plasma using PAFR specific primers without a probe, and the term "qPCR" or "QPCR" refers to quantitative PCR, which can be carried out on tissue samples, on serum and plasma using PAFR specific primers and probes. In controlled reactions, the amount of product formed in a PCR reaction correlates with the amount of starting template (Sambrook, J., E Fritsch, E. and T Maniatis, Molecular Cloning: A Laboratory Manual $3^{rd}$ Cold Spring Harbor Laboratory Press: Cold Spring Harbor (2001). In semiquantitative PCR, quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, such as Sybr Green, and the intensity of staining measured by densitometry. In qPCR, the progression of a PCR reaction can be measured in real time using PCR machines such as the Applied Biosystems' Prism 7000 or the Roche LightCycler which measure product accumulation in real-time. Real-time PCR measures either the fluorescence of DNA intercalating reporter dyes such as Sybr Green into the synthesized PCR product, or the fluorescence released by a reporter dye, such as, but not limited to cy3, cy5, FAM, SYBR Green, HEX™, JOE, TAMRA, Tye™ 563, TEX 615™, Tye™ 665, VIC, and/or LC Red 640, when cleaved from a quencher molecule, where the quencher molecule prevents the reporter dye from being detectable; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the DNA polymerase in the next PCR cycle, releasing the reporter from the quencher molecule, allowing the reporter dye to be detectable. In one variation, known as Scorpion™, the probe is covalently linked to the primer.

Reverse Transcription PCR (RT-PCR) can be used to compare RNA levels in different sample populations, in tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from an animal. The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan qPCR typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, used in real-time qPCR is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

RT-PCR can be performed using commercially available equipment, such as, for example, ABI PRISM 7700 Sequence Detection System (Perkin-Elmer-Applied Biosystems, Foster. City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 Sequence Detection System. The system consists of a thermocycler, laser, charge-coupled device (CCD), camera, and computer. The system amplifies samples in a multi-well format on a thermocycler. During amplification, laser-induced fluorescent signal is collected in real-time through fibre optics cables for each well, and detected at the CCD. The system includes software for running the instrument and for analyzing the data.

5' nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle.

Real-Time Quantitative PCR (qRT-PCR) is a more recent variation of the RT-PCR technique is the real time quantitative PCR, which measures PCR product accumulation through a dual-labeled fluorogenic probe (i.e., TaqMan probe). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996). PCR primers are designed to flank intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the VIMNV for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3' end sequence. In general, optimal PCR primers are generally 17-30 bases in length, and contain about 20-80% G+C bases, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by, reference.

Enzyme-linked immunosorbent assay (ELISA) and sandwich ELISA, are immunoassays that are advantageously used in the methods disclosed herein. In a (direct) ELISA, for example, an unknown amount of antigen (i.e., PAFR nucleotides, PAFR peptides, or PAFR protein) is affixed to a substrate, and then a specific antibody is applied over the surface so that it can bind to the antigen. This antibody is conjugated to a reporter, such as, but not limited to, alkaline phosphatase, peroxidase, β-galactosidase, Atto 425, Atto 488, Cy2, DyLight 405, DyLight 488, Atto 432 Atto 550, Cy3, Cy5, DyLight 549, TEX 615™, Allophycocyanin, Atto 647, DyLight 649, Atto 655, Cy5.5, Dylight 680, and/or DyLight 800, and, in the case of an enzyme being the conjugate, an enzyme, and in the final step a substance is added so that the enzyme can convert to some detectable signal, most commonly a color change in a chemical substrate. In a sandwich ELISA a capture antibody that can bind to the antigen is affixed to the substrate. The other steps are equivalent to the ELISA. The detectable signal can be detected by a number of commercially available systems, such as, but not limited to, the Bio-Rad iMark Readers, BioTek Synergy Readers (Winooski, Vt.), or various BMG LABTECH star Readers (Cary, N.C.).

In an Enzyme Immuno Assay (EIA), which is similar to the sandwich ELISA, streptavidin is affixed to a surface and then the capture antibody is biotinylated, otherwise the other steps are performed equivalently as the ELISA. The EIA immunoassay is advantageously used in the methods disclosed herein. The detectable signal can be detected by a number of commercially available systems, such as, but not limited to, the Bio-Rad iMark Readers, BioTek Synergy Readers (Winooski, Vt.), or various BMG LABTECH star Readers (Cary, N.C.).

In a blotting assay, such as Western Blot, the sample is separated out in an appropriate gel and then transferred to a substrate, such as, but not limited to, nitrocellulose or PVDF. The membrane is then blocked to prevent nonspecific protein binding, followed by incubating the blot with antigen specific antibodies. The antigen specific antibodies can be conjugated with a reporter, such as, but not limited to, alkaline phosphatase, peroxidase, β-galactosidase, Atto 425, Atto 488, Cy2, DyLight 405, DyLight 488, Atto 432 Atto 550, Cy3, Cy5, DyLight 549, TEX 615™, Allophycocyanin, Atto 647, DyLight 649, Atto 655, Cy5.5, Dylight 680, and/or DyLight 800, or can be further bound by a secondary antibody conjugated to a reporter that can bind to the antigen specific antibody. Like in an ELISA, the blot can either be read directly if a reporter dye is conjugated or if an enzyme is conjugated, the appropriate substance is added to the blot in order to create a detectable signal. The signal can them be detected by a number of commercially available systems, such as, but not limited to, the Bio-Rad ChemiDoc (Hercules, Calif.) or a Typhoon Biomolecular Imager (GE Healthcare Life Sciences, Malborough, Mass.).

One of ordinary skill in the art will also understand that PAFR can also be part of high throughput assays. These high throughput assays may not be specifically designed to assay only PAFR, but rather the expression of multiple RNAs, cDNAs, or proteins at once. Example of such high throughput assays include, but are not limited to, spotted oligonucleotide microarrays, printed oligonucleotide microarrays, protein microarrays, single molecule real-time sequencing, ion semiconductor sequencing, pyrosequencing, sequencing by synthesis, sequencing by ligation, nanopore sequencing, chain termination sequencing, tunneling currents DNA sequencing, sequencing by hybridization, sequencing with mass spectrometry, microscopy-based DNA sequencing, RNA polymerase (RNAP) sequencing, and/or in vitro virus high throughput sequencing.

Kits for Assaying

Based on the discoveries of this invention, several types of kits can be envisioned and produced. One embodiment of the kit comprises the primers, reagents, and instructions for assaying PAFR expression using any of the described PCR methods. These kits would comprise: oligonucleotide primers and/or probes labeled with a reporter dye and quencher which specifically bind to PAFR to measure the expression of PAFR; PCR reagents; and instructions for use, either within the kit or available online. Other kits may analysis PAFR protein and comprise: one or more antibody(ies) to PAFR, which may have been conjugated to a reporter as described herein; an optional secondary antibody that binds to the PAFR specific antibody and is has been conjugated to a reporter as described herein; reagents appropriate for the kind of protein capture used, such as ELISA, EIA, or blotting reagents; and instructions for use. The protein kits may optionally further comprise of the substance which corresponds to the conjugated reporter. Alternatively, the kits can further comprise a substrate, such as a glass slide, a multiwell plate, or nitrocellulose paper, which the capture molecule, such as an oligonucleotide or antibody, may be bound to. Optionally, the kit can further comprise any other regent, such as, but not limited to, hybridizing buffer and label, for identification of PAFR in biological samples, using a specific probe. Further kits my assay PAFR in addition to one or more non-PAFR RNA, cDNA, and/or proteins, such as to, but not limited to, housekeeping genes, and would further comprise of capture molecules for the one or more non-PAFR molecules.

A kit to detect BRD sensitive cattle in a population may comprise of a PAFR detection kit as described above and further comprise compounds for inducing expression of PAFR that simulate real-life situations. For example, compounds can simulate transportation stress, such as providing adrenaline, norepinephrine, and/or cortisol in physiological concentrations. Such physiological concentrations of norepinephrine would include a final concentration in a sample of about 75 to about 125 pg/mL, or more preferably final concentrations of about 90 to about 110 pg/mL, and even more preferably final concentrations of about 95 to about 105 pg/mL. Physiological concentrations of cortisol in a sample would include final concentrations of about 3 to about 7 ng/mL, or more preferably final concentrations of about 4 to about 6 ng/mL, or even more preferably final concentrations of about 4.5 to about 5.5 ng/mL. Optionally, the kit could comprise compounds which simulate a bacterial challenge, such as but not limited to, physiological concentrations of intact, lysed, static, and/or bacterial components. Physiological concentrations of intact, lysed, static, and/or bacterial components would be a final concentration of about $10^4$ to about $10^8$ CFUs/mL, or about $10^5$ to about $10^7$ CFUs/mL, or more preferably about $10^6$ CFUs/mL. Alternatively, a BRD detection kit could comprise both transportation stress and bacterial challenge simulators.

Systems for Assaying

A "system" as used herein refers to a sample, a kit, and a device to detect the signal produced by the kit. The sample may be drawn blood, a tissue biopsy, lung lavage, sperm, the kit may be any of the kits contemplated herein, and the device may include any of the variety of available for the various assay methods described herein. For example, for detecting the bands resulting from semiquantitative PCR, an image may be taken using a camera, and the bands quantified using software such as, but not limited to, ImageJ Bethesda, Md.). ImageJ may also be used to quantify the bands created during blots, such as, but not limited to, Western blotting.

Florescent reporters can be read on systems such as, but not limited to, ABI PRISM 7700 Sequence Detection System or Lightcycler for PCR based assays, or on a Bio-Rad ChemiDoc or a Typhoon Biomolecule Imager for blots. ELISA and EIA can be read on devices such as, but not limited to, the Bio-Rad iMark Readers, BioTek Synergy Readers, or various BMG LABTECH star Readers.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Identification of Pro-Inflammatory Mediator Associated with BRD Susceptibility. Sampling of calf blood samples to confirm the pro-inflammatory mediator of BRD was conducted. Approximately 5 mL of whole blood was collected from the jugular or caudal vein of non-transported juvenile cattle (n=260). Blood was placed in EDTA tubes, and either cortisol (5 ng/mL) or norepinephrine (100 pg/mL) was added to the blood. After an overnight incubation at 37° C. with gentle rolling, half of the blood was used for total RNA isolation followed by a semi-quantitative RT-PCR protocol using 50 ng of RNA and a PAFR forward primer 5'-atggagccaaataattccttt-3' (SEQ ID NO: 4) and reverse primer 5'-ctaatatttgagggatttg-3' (SEQ ID NO: 5). Half of the blood was used for second messenger analysis and half was used for PAFR expression analysis. Approximately 10% of blood samples (which further correlates to the approximate incidence of BRD based on USDA data) yielded visible PAFR transcript-specific amplicons after 10-15 PCR cycles, while 80% of the samples did not yielded an amplicon after 40 cycles of RT-PCR (see FIG. 1). PAFR gene expression also increased in a stress hormone concentration-dependent manner. Data were standardized based on second messenger accumulation production in the presence of vehicle. Expression of PAFR is presented as the number of RT-PCR cycles required to visualize an amplicon on an agarose gel. Amplicons were visible at 10, 15, 20, 25, 30, 35, and 40 cycles, i.e., no amplicons were visible after only 5 cycles and most samples (n=202) did not yield an amplicon after 40 cycles (latter arbitrarily ascribed with 45 as the number of cycles).

The results confirm PAFR has in increase in expression in response to stress hormones in some cattle as shown in FIG. 1 depicting the relationship between PAFR expression and second messenger accumulation in individual bovine blood samples incubated with commensal oral bacteria and stress hormones. Each square represents a sample from a single animal. A linear regression line, using the least squares model, is presented (slope=−0.76). The PAFR is hyper expressed in response to stress hormones in some cattle.

Association between PAFR hyper expression and the intracellular accumulation of a second messenger in response to a specific commensal oral bacterium. Blood was drawn from cattle as described. After incubation with stress hormones, the other half of the blood sample was subjected to second messenger accumulation assays in response to $10^6$ CFUs/mL of an oral commensal bacterium. As shown in FIG. 1, stress hormone- and commensal oral bacteria-mediated second messenger accumulation correlated with PAFR hyper expression. This response was dependent on the concentration of stress hormones and the concentration of commensal oral bacteria (not shown). The PAFR has an increase in expression in response to stress hormones in some cattle and there is an association between an increase in PAFR expression and the intracellular accumulation of a second messenger in response to a specific oral commensal bacterium. The data indicate that approximately 10% of calf blood samples (n=260) exhibited a stress hormone- and commensal oral bacteria-dependent increase of PAFR gene expression coinciding with intracellular second messenger accumulation.

The emphasis on PAFRi for treatment of BRD is supported by these findings, along with the recognition that inactivating mutations in the PAFR has resulted in decreased susceptibility to pneumonopathies in humans, and that human ortholog of the PAFR elicits an inflammatory response that is analogous to the lung pathology associated with BRD. The confirmation in this Example that commensal oral bacteria interact with the PAFR and these bacteria are present in the lungs of cattle with BRD, along with PAFR expressed in the lungs and in blood cells—the latter finding allowing for blood-based screening of mechanisms underlying BRD pathogenesis confirm the necessity for anti-inflammatory treatments for BRD. Moreover, the activity of the PAFR can be pharmacologically inhibited which will provide the basis for the drug efficacy studies described herein.

These preliminary results suggest a triad between three established components of BRD: stress, bacteria, and inflammation. Stress is known to accentuate bacteria growth and inflammation, while also modulating gene expression. Additional testing described herein further confirms all three of these components, ultimately implicating a druggable PAFR that has not been previously identified and/or employed as a mediator of BRD.

Example 2

Figure 2:
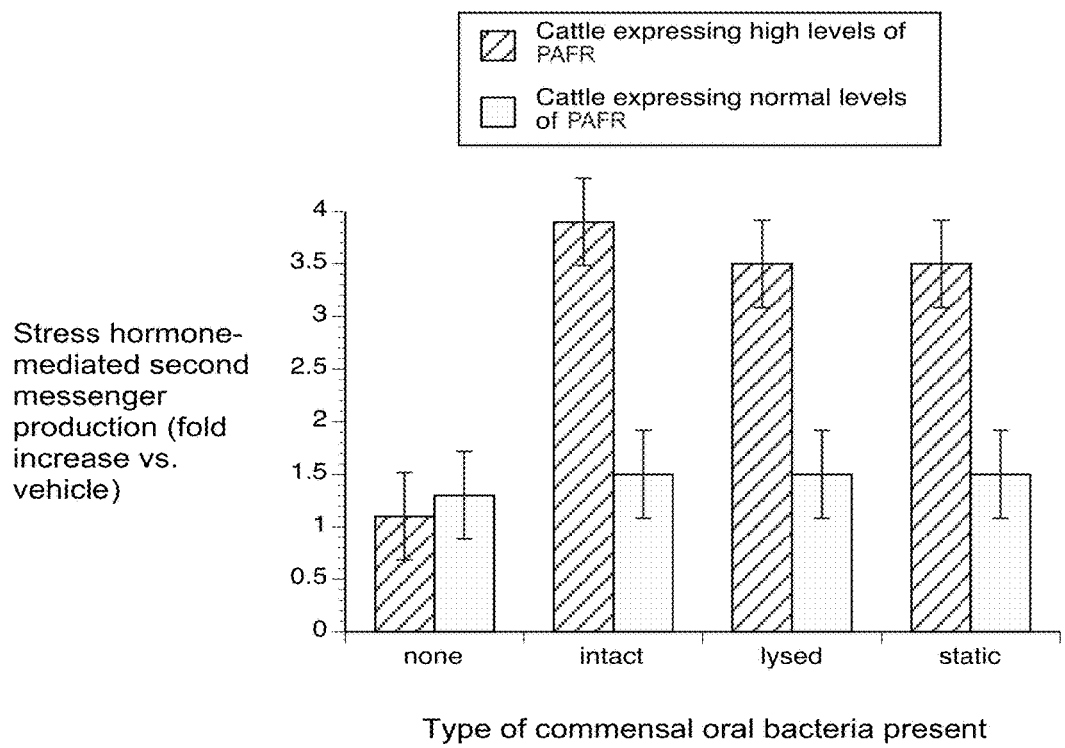
FIG. 2 shows PAFR expression in relation to a second messenger accumulation in individual bovine blood samples incubated with various types of commensal oral bacteria as detailed in Example 2.

Lysed or inactivated commensal oral bacteria activate PAFR-dependent second messenger accumulation in calf blood cells that hyper express the PAFR. The studies of Example 1 were repeated except that lysed or inactivated commensal oral bacteria were substituted for live bacteria. Bacteria were either lysed with a bactericidal antibiotic used clinically against BRD (ceftiofur) or inactivated by a bacteriostatic antibiotic used clinically against BRD (tulathromycin). As shown in FIG. 2, second messenger accumulation was statistically higher in hyper expressing samples incubated with lysed or inactivated bacteria, when compared to cells with normal or no expression of the PAFR.

As outlined in Example 1, blood was taken from 10 animals deemed to hyper express PAFR (as identified in experiments presented in FIG. 1) and 10 animals deemed to express "normal" levels of PAFR. Approximately 5 mL of whole blood was collected from the jugular or caudal vein of non-transported cattle. Blood was placed in EDTA tubes, and cortisol (5 ng/mL) and norepinephrine (100 pg/mL) were added to the blood that was transported overnight on ice. The next day, 3.5 mL of each blood sample was aliquoted into seven different tubes that were incubated with 0 or $10^6$ CFUs/mL of bacteria (intact, lysed, or static), along with a reagent for second messenger analysis, for six hrs at 37° C. with gentle rolling. As vehicle controls, ceftiofur (32 µg/mL) and tulathromycin (50 µg/mL) were used since these two drugs served as the lysing and static agents, respectively. After the six-hour incubation period, blood samples were analyzed for the production of second messengers. Data was standardized based on second messenger production in the presence of vehicle. Data are presented as the mean+sem for 10 animals at each concentration. For the remaining 1.5 mL of blood samples, total RNA was isolated using the RNEasy Blood kit. Fifty ng of total RNA was then subjected to semi-quantitative RT-PCR to confirm the PAFR expression status of each animal, as described in Example 1.

The data confirmed lysed or inactivated commensal oral bacteria activate PAFR-dependent second messenger accumulation in calf blood cells that show an increase in expression of PAFR. This data confirms a rationale for existing/prior antibiotic failures in treating BRD and demonstrating preferred efficacy of the methods of treatment according to the invention.

Example 3

A PAFR inhibitor blocks the stress hormone- and commensal oral bacteria-mediated second messenger accumulation in calf blood cells that have an increase in expression of PAFR. Studies presented in Example 1 and FIG. 1 were repeated with the inclusion of the compositions comprising the anti-inflammatory drug rupatadine according to the invention. Blood was drawn from 10 animals that have an increase in PAFR expression (those in which an RT-PCR amplicon was visible after 10-15 cycles) and 10 animals with "normal" or no PAFR expression (those in which an RT-PCR amplicon was visible after 30-45 cycles).

Figure 3:
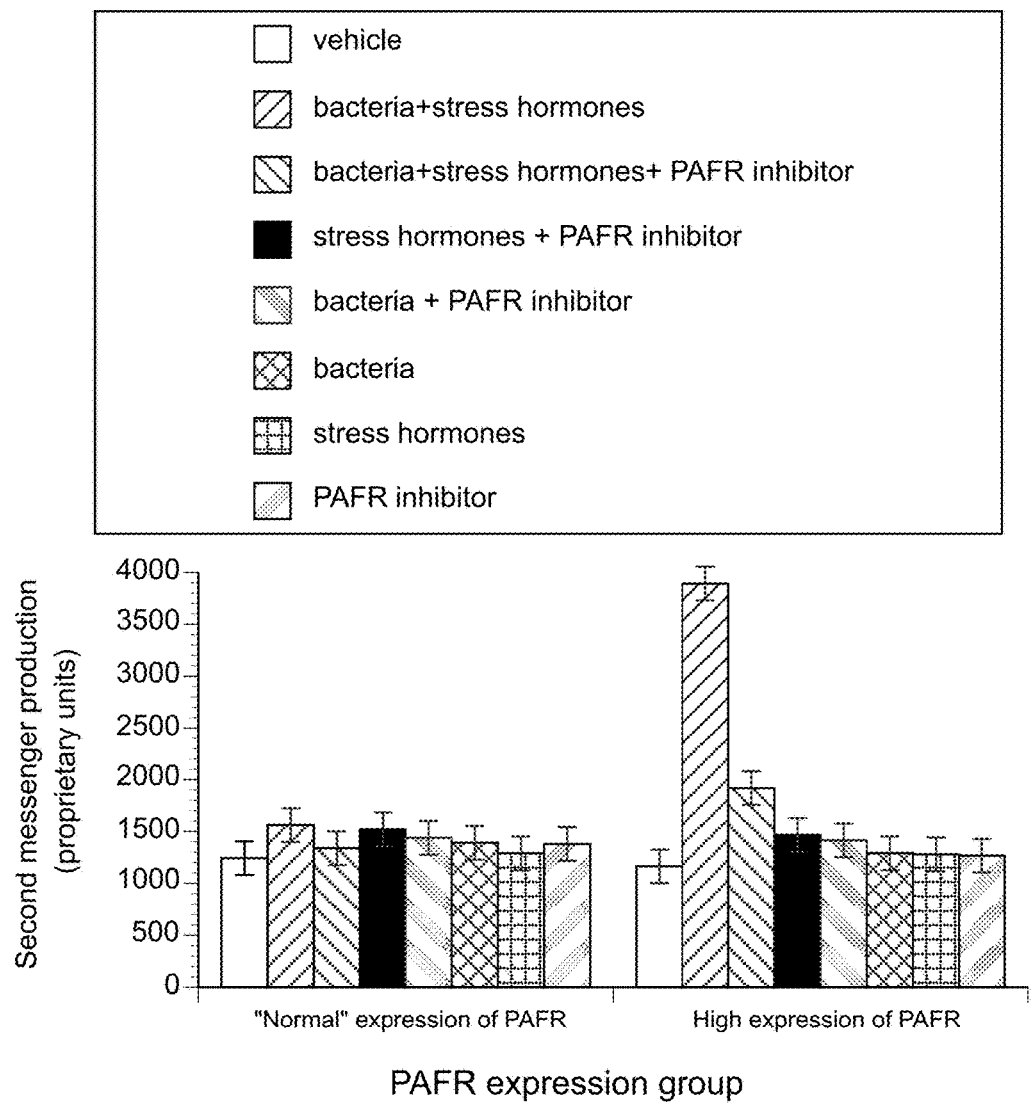
FIG. 3 shows PAFR expression groups as detailed in Example 3 according to embodiments of the invention.

Approximately 5 mL of whole blood was collected from the jugular or caudal vein of non-transported juvenile and adult cattle. Blood was placed in EDTA tubes, aliquoted, and cortisol (5 ng/mL) and norepinephrine (100 pg/mL) were added to some of the blood. The next day, blood samples were incubated with 0 or $10^6$ CFUs/mL of commensal oral bacteria, 0 or 500 nM of the inhibitor, and a second messenger reagent for six hours at 37° C. with gentle rolling. After the six-hour incubation period, blood samples were analyzed for the production of second messengers. Data was standardized based on second messenger production in the presence of vehicle. Data are presented as the mean+sem for 10 animals at each concentration. For the remaining blood, total RNA was isolated using the RNEasy Blood kit. Fifty ng of total RNA was then subjected to semi-quantitative RT-PCR to confirm the PAFR expression status of each animal. As shown in FIG. 3, second messenger accumulation was statistically higher in samples which have an increase in PAFR when the PAFRi was absent, but indistinct from normal or non-expressing samples when the PAFRi was present.

Example 4

The studies set forth in Examples 1-3 support the mechanism of action in the BRD pathology, that increased PAFR expression is associated with the development of BRD at the feedlot. Additional data was obtained from the acquisition of 3,695 blood samples from calves arriving at four different feedlots in Nebraska and Kansas (details shown in Table 2). Upon arrival at the feedlot, 5 mL of blood was taken from the caudal vein of which 3 mL was injected into the PAXGene RNA Blood tube (PreAnalytix). PAXGene RNA Blood tubes were immediately shipped on dry ice for RNA isolation. High-quality RNA was isolated in 3,695 samples that were subjected to qRT-PCR targeting a candidate gene (PAFR) identified as a potential drug target in previous studies. The UBC gene was empirically determined to be an appropriate housekeeping gene in these samples, and thus it was also the target of a qRT-PCR assay using primers purchased from QIAGEN (Cat. no. PPB01883A). In the six weeks following blood collection, which as outlined according to the invention is a BRD susceptibility period, feedlots kept track of and reported the individual animals that developed BRD. An animal was ascribed as BRD(+) if it presented with abnormal lung sounds (identified using the Whisper stethoscope), rhinorrhea, ocular discharge, coughing, dyspnea, anorexia, pyrexia, or listlessness and required antibiotic therapy. Animals free of these signs and not receiving treatment for respiratory disease were designated as BRD-free. As shown in Table 1, the BRD incidence was 15.3% during the six-week time period.

TABLE 1

| Feedlot | Number of BRD (+) cattle/total number of cattle sampled | Average daytime and nighttime temperatures during the BRD susceptibility period | Cattle breed profiles (80% Angus is the industry average) | Cattle gender profile | Average distance that cattle traveled to reach the feedlot | Metaphylactic antibiotic used upon arrival at the feedlot; unique husbandry practices |
|---|---|---|---|---|---|---|
| NE1 | 41/994 | 80° F. and 49° F. | 80% Angus and 15% Charolais | 65% female | ~300 miles | tilmicosin |
| NE2 | 334/1001 | 74° F. and 52° F. | 80% Angus, 10% Charolais, and 10% Hereford | 72% male | ~1,000 miles | tulathromycin; autogenous bacterin, Calvary 9, ivermectin, band castration, implant, and BoviShield V |
| KS1 | 99/1051 | 90° F. and 72° F. | 90% Angus | 72% female | ~450 miles | tildipirosin |
| KS2 | 91/649 | 88° F. and 75° F. | 60% Angus and 30% Charolais | 53% male | ~500 miles | gamithromycin to a portion of calves |

Figure 4:
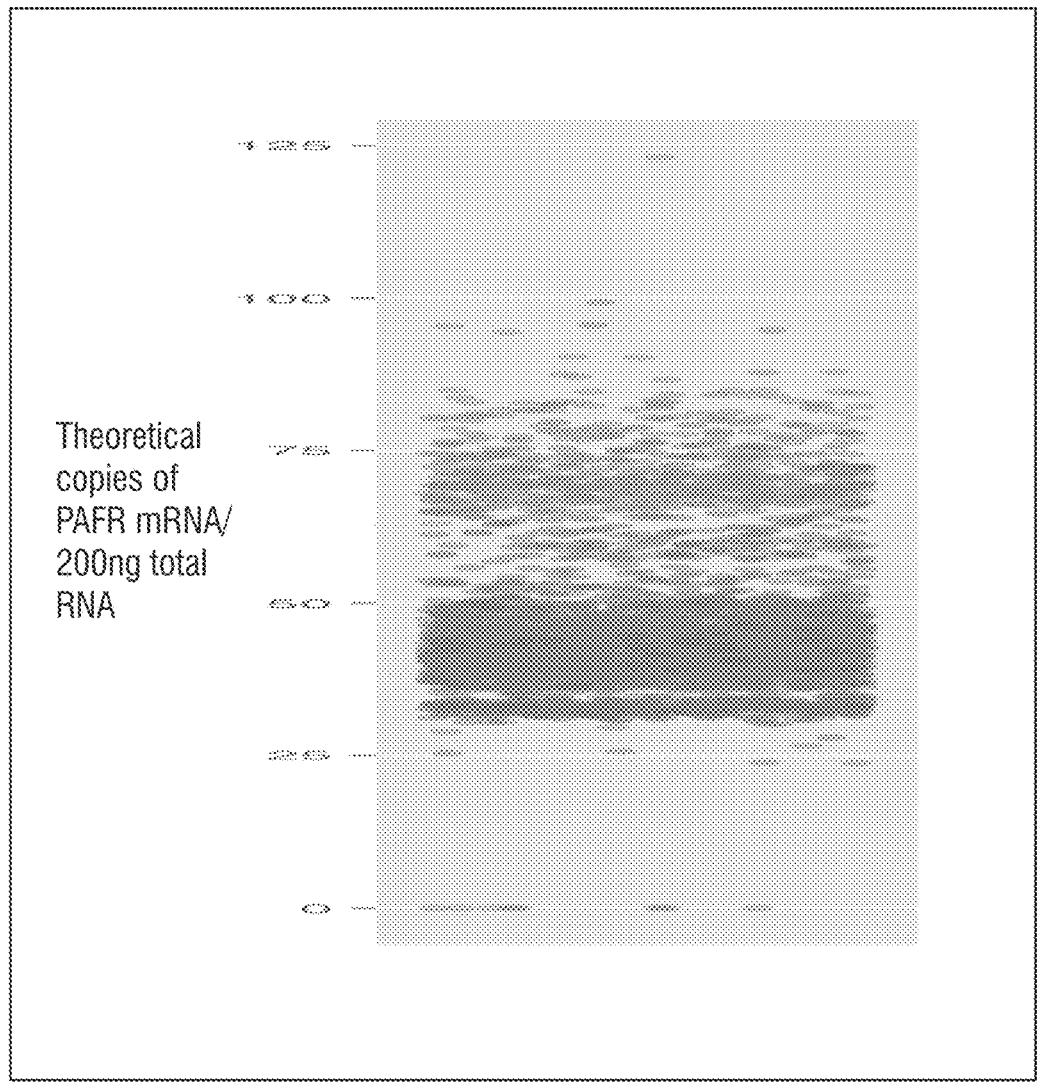
FIG. 4 shows PAFR hyper expression as a predictor to BRD according to embodiments of the invention.

All 3,695 RNA samples were subjected to qRT-PCR targeting the transcript for PAFR. As shown in FIG. 4, there was a correlation between PAFR expression and BRD and this correlation was determined to be 0.7 based on logistic regression analysis. Expression of the UBC transcript was limited to 19-27 theoretical copies of mRNA/200 ng total RNA in most samples.

Further assessment was completed to confirm that PAFR expression is increased in the lungs of calves that died from BRD. Three of the seven calves that developed BRD in a prior feedlot study died from the ailment. Total RNA was isolated from the diseased (consolidated) lungs and then was subjected to the semi-quantitative RT-PCR. Amplicons were visible after 10-15 cycles in all three samples. During the same time period, three animals died from diseases unrelated to BRD (bloat, lightning strike, and thromboembolic meningoencephalitis) and their normal-appearing lungs were collected for RNA isolation and RT-PCR analysis. Amplicons were visible after 30-45 cycles in these samples as outlined further in Table 2 providing assessment of PAFR expression, using semi-quantitative RT-PCR, in the lungs of calves that died from BRD. RNA was isolated using the RNEasy kit and the RT-PCR was performed as described in Example 1. Data presented are the mean+sem, using three replicates per animal.

TABLE 2

| Presumed cause of death | Number of RT-PCR cycles required to visualize an amplicon |
| --- | --- |
| BRD | 13.3 ± 1.7 |
| BRD | 10 ± 0 |
| BRD | 11.7 ± 1.7 |
| Bloat | 40 ± 5 |
| lightning strike | 36.7 ± 3.3 |
| thromboembolic meningoencephalitis | 41.7 ± 3.3 |

Figure 5:
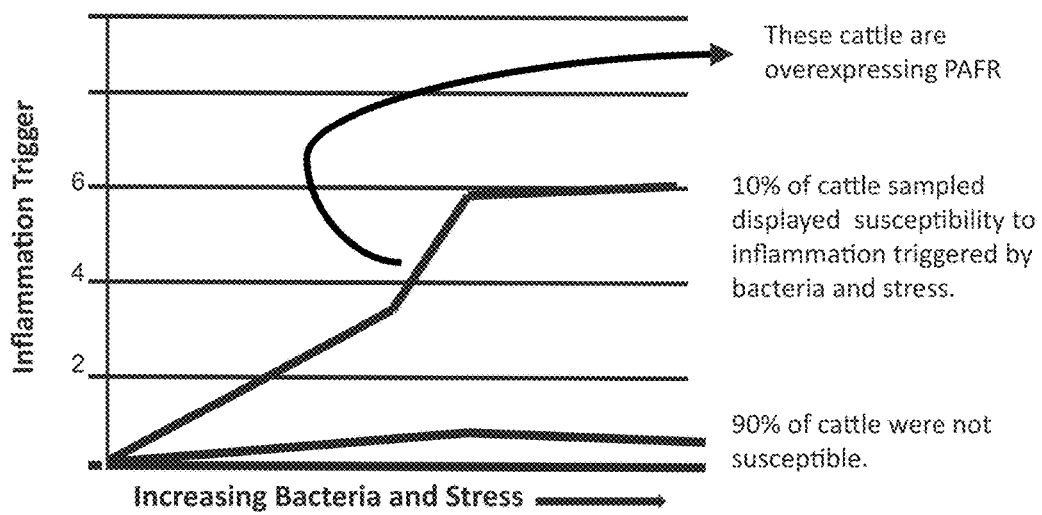
FIG. 5 shows PAFR expression and BRD susceptibility correlation as detailed in Example 4 according to embodiments of the invention.

The data further confirms PAFR expression was increased in the lungs of calves that died from BRD. Still further, additional data was collected from isolated protein from the lungs and confirmed that the PAFR protein was more abundant in BRD calves as per a Western blot. A further graphical depiction of this correlation is shown in FIG. 5 with 10% of cattle sampled displaying susceptibility to inflammation triggered by bacteria/stress, as opposed to 90% of the sampled cattle not susceptive based on the measurement of the inflammation trigger PAFR.

Figure 10:
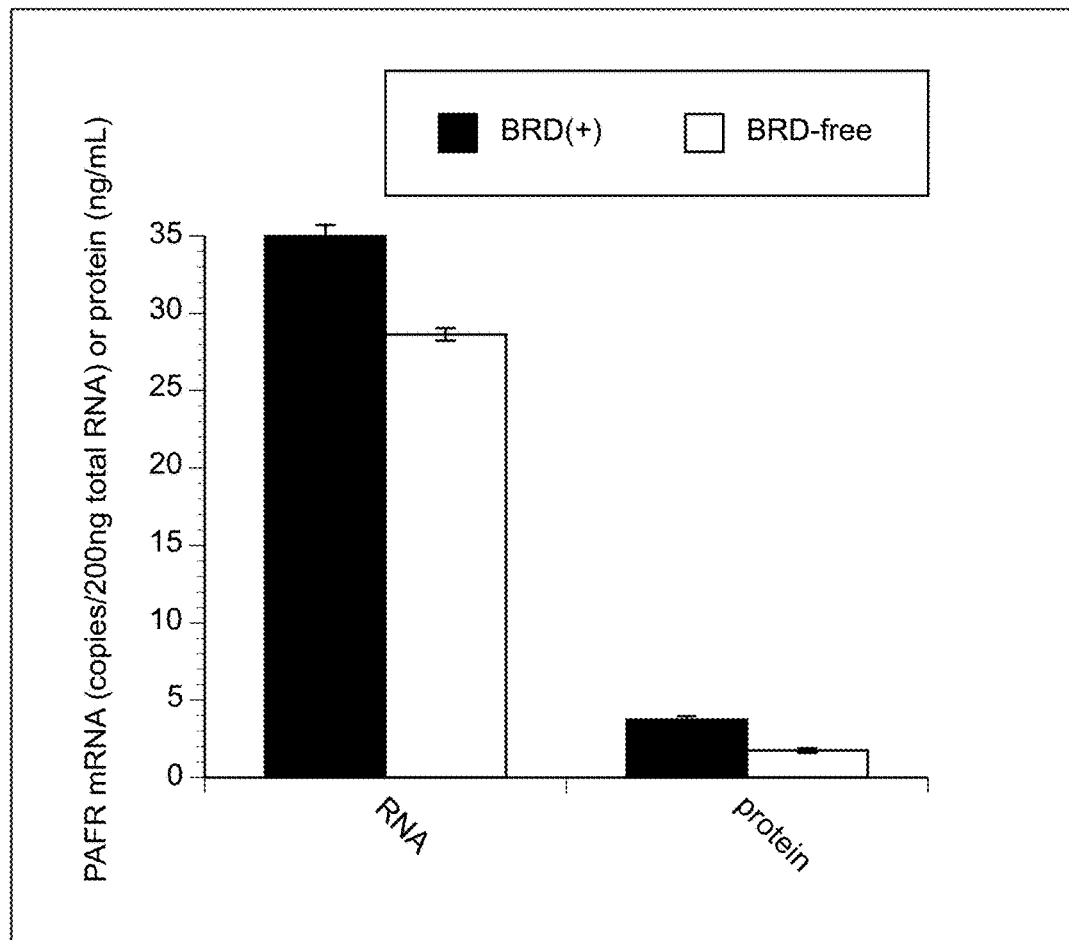
FIG. 10 shows the relationship between PAFR mRNA and PAFR protein levels in calves that develop BRD and calves that are BRD-free.

Additional evaluation was performed to confirm the correlation of PAFR expression in BRD positive and BRD free population. A total of 300 calves were assayed as the they entered a feedlot. Blood samples were collected and PAFR mRNA and PAFR protein were analyzed. RNA was isolated from blood and quantitative RT-PCR targeting the mRNA encoding PAFR (SEQ ID NO: 1) performed to determine PAFR mRNA levels. In addition, protein was isolated and subjected to ELISA to quantitate the amount of PAFR protein. The data was then segregated based on the clinical BRD outcome, i.e., development of BRD (BRD(+)) or the absence of BRD (BRD-free) within the first six weeks of arrival at the feedlot. The graphical depiction is shown in FIG. 10, with elevated levels of both PAFR mRNA and PAFR protein in the calves whom developed BRD.

Example 5

An initial study was performed to confirm BRD prevention at the feedlot using an anti-inflammatory composition comprising rupatadine, the oral inhibitor of PAFR. A total of 18 calves were evaluated with the treatment arm receiving a dosage rate of 0.3 mg/kg. Calves were provided the drug in the feed during the first three weeks after entering the feedlot which is within the high risk 6-week period following transfer of the animal. Calves were purchased from a location in Joplin, Mo. having an overall incidence of BRD at >40% which is higher than the standard incidence of about 10% in cattle.

Figure 6:
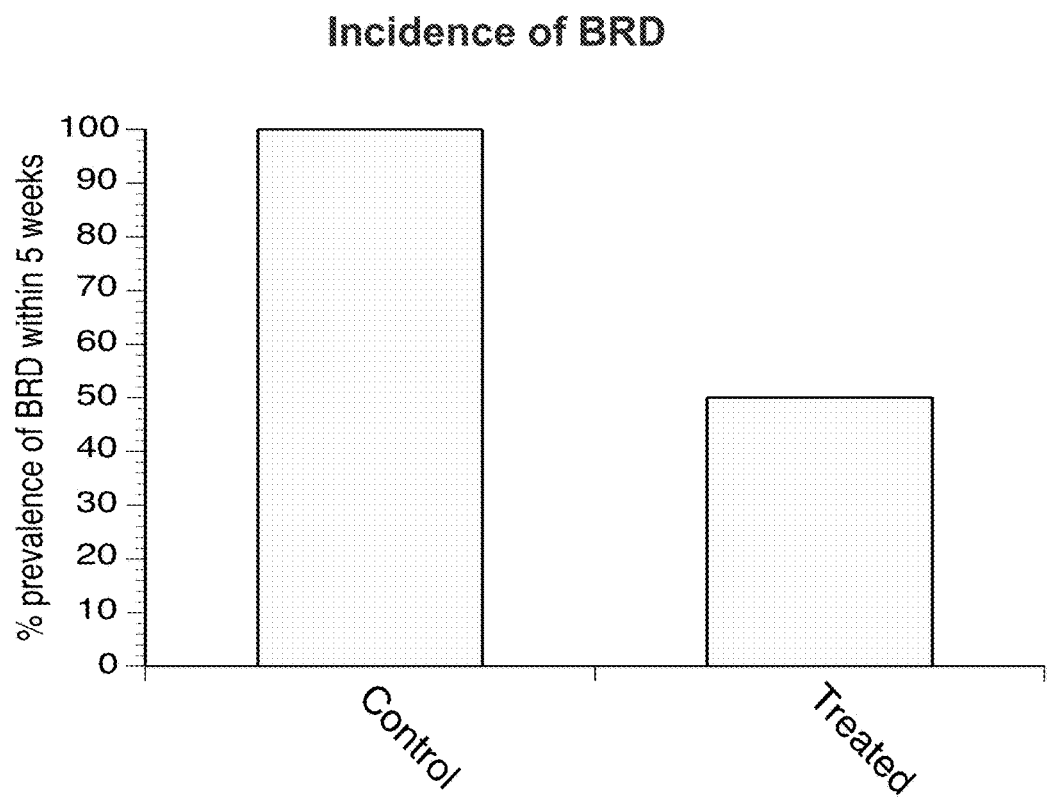
FIG. 6 shows the incidence of BRD in calves treated with the composition according to an embodiment of the invention, wherein the oral administration of the drug led to a decreased incidence of BRD in eight calves compared to 10 calves that did not receive the composition.

FIG. 6 shows the incidence of BRD of the calves treated with the drug. As shown oral administration of the drug led to a decreased incidence of BRD in the 8 calves evaluated compared to the 10 calves that received no drug (which had 100% prevalence of BRD within 5 weeks) as opposed to 50% of the treated calves. The data shows a 50% reduction in BRD according to the methods of prevention of the present invention. A skilled artisan will appreciate the standard of care may include concomitant treatment with an antibiotic in addition to the anti-inflammatory agent rupatadine as the pathology of BRD includes both pathogenic and inflammatory components and the efficacy in prevention of BRD would be increased.

Example 6

A further study was performed to confirm BRD prevention at the feedlot using the anti-inflammatory composition comprising rupatadine. The same methodology of Example 5 was employed with the modification of the number of calves and the dosage rate. The dosage rate was increased to 0.6 mg/kg. The number of calves were increased to 24 in total. The results are consistent to the first trial, including: 41.7% of treated calves (n=5 of 12) developed BRD whereas 100% of untreated calves (n=12 of 12) developed BRD.

Consistent with the conclusions of Example 6, a skilled artisan will appreciate the standard of care may include concomitant treatment with an antibiotic in addition to the anti-inflammatory agent rupatadine as the pathology of BRD includes both pathogenic and inflammatory components and the efficacy in prevention of BRD would be increased.

Example 7

A further study was performed to confirm BRD prevention at the feedlot using the anti-inflammatory composition comprising rupatadine as outlined in Example 5 with the modification of the number of calves (20 total) and the dosage rate. The dosage rate increased to 1.2 mg/kg. The results were consistent with the first and second trials, and demonstrated additional benefit, including: 33.3% of treated calves (n=3 of 10) developed BRD whereas 100% of untreated calves (n=10 of 10) developed BRD.

Example 8

Figure 7:
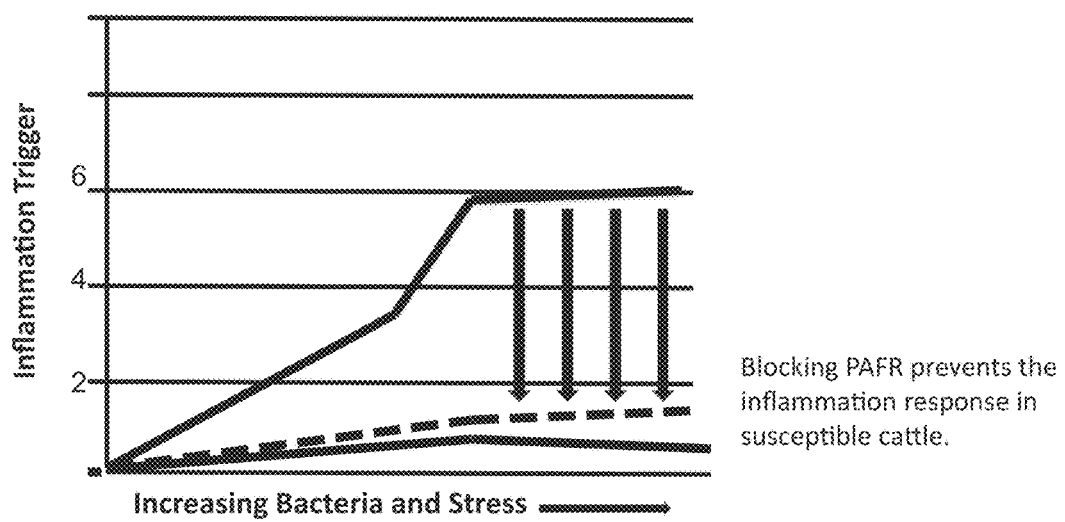
FIG. 7 shows the effects of an anti-PAFR composition according to embodiments of the invention, wherein the composition prevents the bacteria and stress hormone-induced inflammation.
Figure 8:
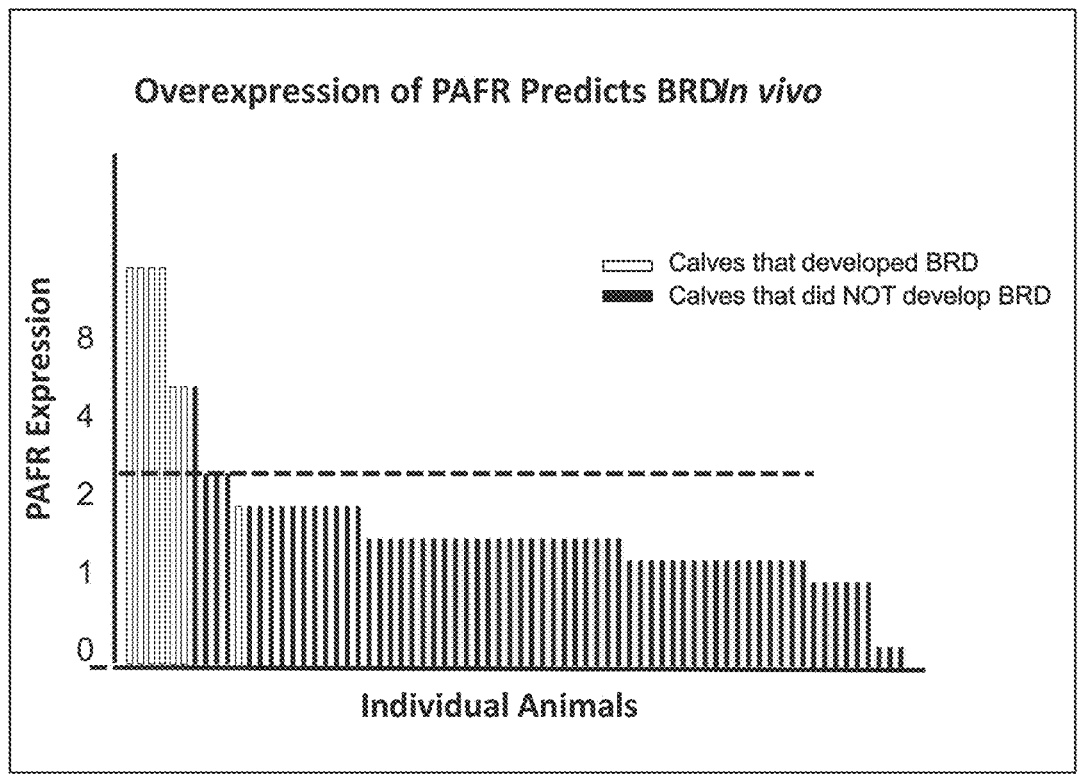
FIG. 8 shows the PAFR overexpression and predictive outcome of BRD in vivo according to embodiments of the invention.

The results in Examples 5-6 are further illustrated in FIG. 7, showing the effects of the anti-PAFR composition, wherein the composition prevents the bacteria and stress hormone-induced inflammation. In addition, FIG. 8 correlates the PAFR overexpression and predictive outcome of BRD in vivo following the assessment of PAFR expression levels in 73 calves on exit of a transportation vehicle and thereafter tracked in the following six weeks during the stress period to monitor the development of BRD. As shown of the 7 calves overexpressing PAFR upon existing the transport vehicle all but one developed BRD, whereas of the 66 calves showing normal PAFR expression only one developed BRD.

Example 9

Figure 9:
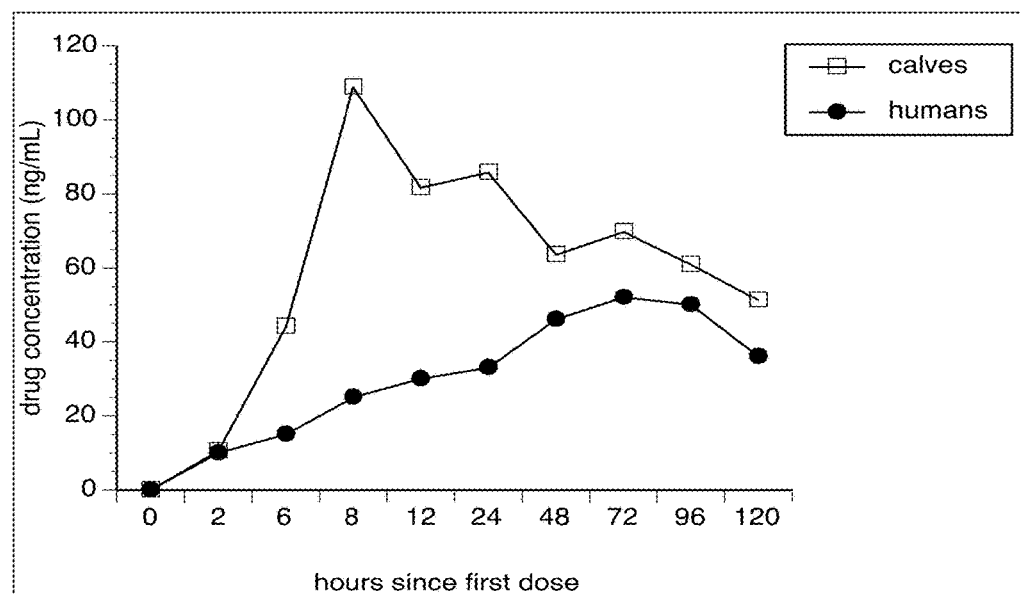
FIG. 9 shows the results of the pharmacokinetics study as detailed in Example 8 according to embodiments of the invention.

A pharmacotherapeutic study was completed to confirm the PAFRi survives the rumen and reaches therapeutic blood and lung concentrations following oral administration to feedlot calves. Six calves were purchased and given daily oral doses of 30 mg/animal of the drug rupatadine for 5 days. Blood was drawn five times on day one and twice per day thereafter to measure the blood levels of rupatadine. The results are shown in FIG. 9, illustrating the drug reaches therapeutic concentrations more rapidly than in humans.

In addition to the blood levels of the drug, the amount of the drug in the muscle tissue is also analyzed. Six recently weaned feedlot calves were orally dosed with 50 mg of rupatadine once a day for five days, a dose that was determined based on allometric scaling from human data. Blood samples were taken at 0, 2, 4, 8, 12, 24, 48, 72, 96, and 120 hours after the first dose. Calves were euthanized at the 120-hour time point at which lungs samples were removed. Samples were submitted to the PhAST laboratory at Iowa State University, for LCMS-based quantitation of the drug and its primary metabolite that is pharmacologically active.

Example 10

Predicted protein alignment of the human platelet-activating factor (sequence ID: NP_000943.1; SEQ ID No: 3) ("Query") and the bovine platelet-activating factor (Subject, "Sbjct") (sequence ID: XP_005203219.1; SED ID No: 2). FIG. 24 shows the two proteins are 85% identical, i.e., 85% of the amino acids are exactly the same. The two proteins are 91% similar, i.e., 91% of the amino acids are either identical or similar such as Isoleucine ("I") and Valine ("V"). The sequence in between illustrates the identical amino acids, the similar amino acids ("+"), and the dissimilar amino acids (blank spaces). Both proteins are 341 amino acids in length.

Bos taurus platelet-activating factor mRNA, NCBI Reference Sequence: XM_0052031623
(SEQ ID NO: 1)
atgaccagcc tctacttcca gcacatagag atggagccaa ataattcctt tcgtgtggac tcagagttcc gatacaccct cttcccaatt ttttacagca tcgtctttgt gctgggggtc attgccaaca gctacgtgct gtgggtcttt gcccgcttgt acccttccaa gaaattcaac gagataaaga tcttcatggt gaacctcacc atggctgacc tgctcttctt ggtcaccctg cccctgtgga tcgtctacta ctacaaccag ggtgactgga ttcttcccaa attcctgtgc aacctggctg gctgcttctt cttcattaac acctactgct cagtggcctt cctggctgtc atcacttaca accgcttcca ggcagtgaca aggcccatca agactgctca ggctaccacc cgaaagcgtg gcatccttct gtccctgatt atctgggtgt ccattgtggg cgcagcatcc tacttcttcg tcctggactc gaccaacagg gagcccaaca agactggctc agccaacatc acacgctgct ttgaacatta cgagaagggc agcatcccgg tcctcaccat ccacatcttc ctggtgttca gcttcttcct cgtcttcctc atcatcctct tttgcaactt ggtcatcatc cgcacgctgc tcacgcagca ggtgcaaata cagcgcaacg ccgaggtcaa gcgccgggcg ctctggatgg tctgcactgt cctggctgtg ttcatcatct gtttcgtgcc ccaccacctc gtgcagctgc cctggaccct ggccgagctg ggcttccagg acaccgactt ccaccaggcg attaacgatg cacatcaggt cactctctgc ctccttagta ccaactgtgt cttagacccc attatctact gtttcctcac caagaagttc cgcaagcacc tcaccgagaa gttgtacagt atgcgcgaga gccggaagtg ctcccgggcc acctcggaga cgggcacgga agtggtcatg cagctcaaag atgtccctgt caaatccctc aaatattag Bos Taurus platelet activating factor protein,
NCBI Reference Sequence: XP_005203219.1;
SEQ ID NO: 2
MISLYFQHIEMEPNNSFRVDSEFRYTLFPIFYSIVFVLGVIANSYVLWVF

ARLYPSKKFNEIKIFMVNLTMADLLFLVTLPLWIVYYYNQGDWILPKFLC

NLAGCFFFINTYCSVAFLAVITYNRFQAVIRPIKTAQATTRKRGILLSLI

IWVSIVGAASYFFVLDSTNREPNKTGSANITRCFEHYEKGSIPVLTIHIF

LVFSFFLVFLIILFCNLVIIRILLTQQVQIQRNAEVKRRALWMVCIVLAV

FIICFVPHHLVQLPWILAELGFQDTDFHQAINDAHQVILCLLSINCVLDP

IIYCFLIKKFRKHLTEKLYSMRESRKCSRATSEIGTEVVMQLKDVPVKSL

KY

Homo sapiens platelet activating factor protein,
NCBI Reference Sequence: NP_000943.1;
SEQ ID NO: 3
MEPHDSSHMDSEFRYTLFPIVYSIIFVLGVIANGYVLWVFARLYPCKKFN

EIKIFMVNLIMADMLFLITLPLWIVYYQNQGNWILPKFLCNVAGCLFFIN

TYCSVAFLGVITYNRFQAVIRPIKTAQANTRKRGISLSLVIWVAIVGAAS

YFLILDSTNIVPDSAGSGNVIRCFEHYEKGSVPVLIIHIFIVFSFFLVFL

IILFCNLVIIRILLMQPVQQQRNAEVKRRALWMVCIVLAVFIICFVPHHV

VQLPWILAELGFQDSKFHQAINDAHQVILCLLSINCVLDPVIYCFLIKKF

RKHLTEKFYSMRSSRKCSRATIDTVIEVVVPFNQIPGNSLKN

Example 11

Figure 11:
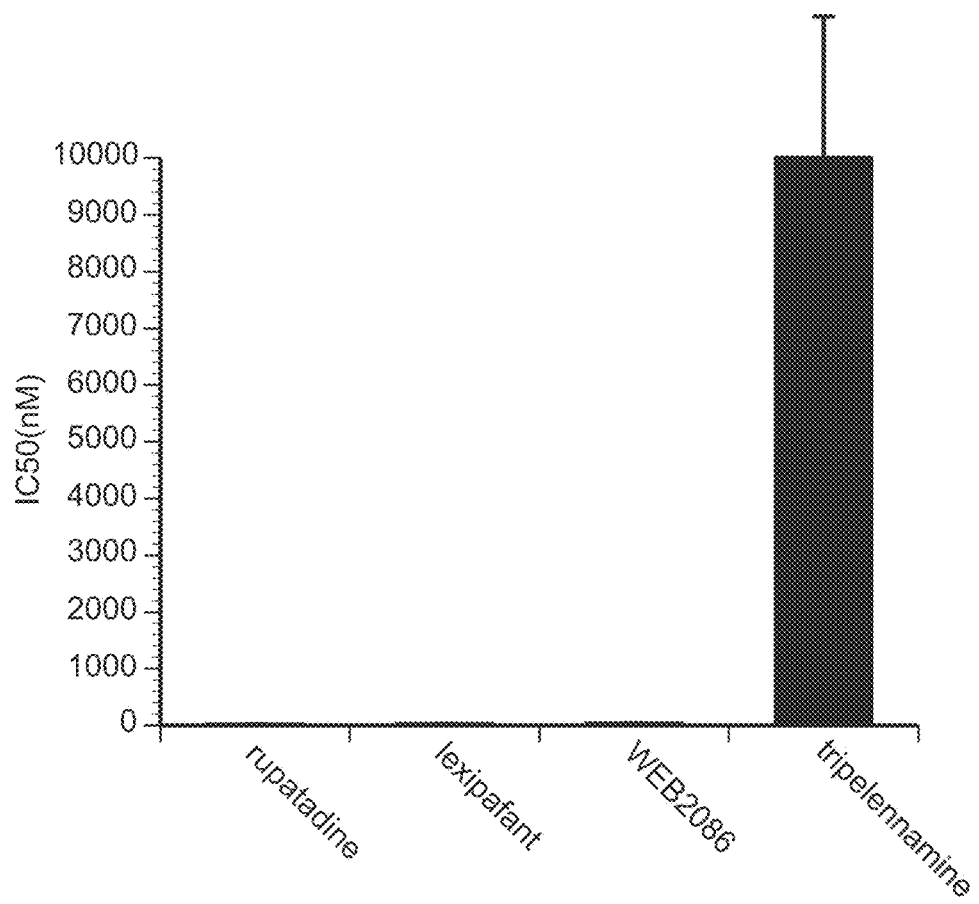
FIG. 11 shows bovine PAFR expression being blocked by the administration of rupatadine and two other classic PAFR antagonists, lexipafant and WEB2086. Bovine PAFR is not blocked by tripelennamine, a bovine approved antihistamine.

Bovine PAFR was cloned into pcDNA3.3 expression vector and transiently expressed in BHK tissue culture cells using lipofectamine as per Carlson et al., J Biol Chem, 271:23146053 (1996), herein incorporated by reference in its entirety. Ten nM PAF was then added to the cells in the presence of various concentrations of various antagonists: rupatadine, lexipafant (as in Kingsnorth, et al., BJS, 82:1414-20 (1995), herein incorporated in its entirety), and WEB2086 a PAF antagonist which has not been commercialized and/or used in humans to date (as in Casals-Stenzel et al., J of Pharmacolo Experimental Therapeutics, 241:974-81 (1987), herein incorporated in its entirety), as well as tripelennamine, a bovine-approved antihistamine at concentrations ranging between 1-100 nM. Intracellular calcium accumulation was monitored in the transfected cells using a commercially available kit (Abcam, Cambridge). $IC_{50}$ values were then determined by identifying the concentration of the antagonist that reduced the maximal PAF-mediated intracellular calcium accumulation by 50%. As shown in FIG. 11, bovine PAFR function is blocked by rupatadine and the other PAFR antagonists, but not the antihistamine.

Figure 12:
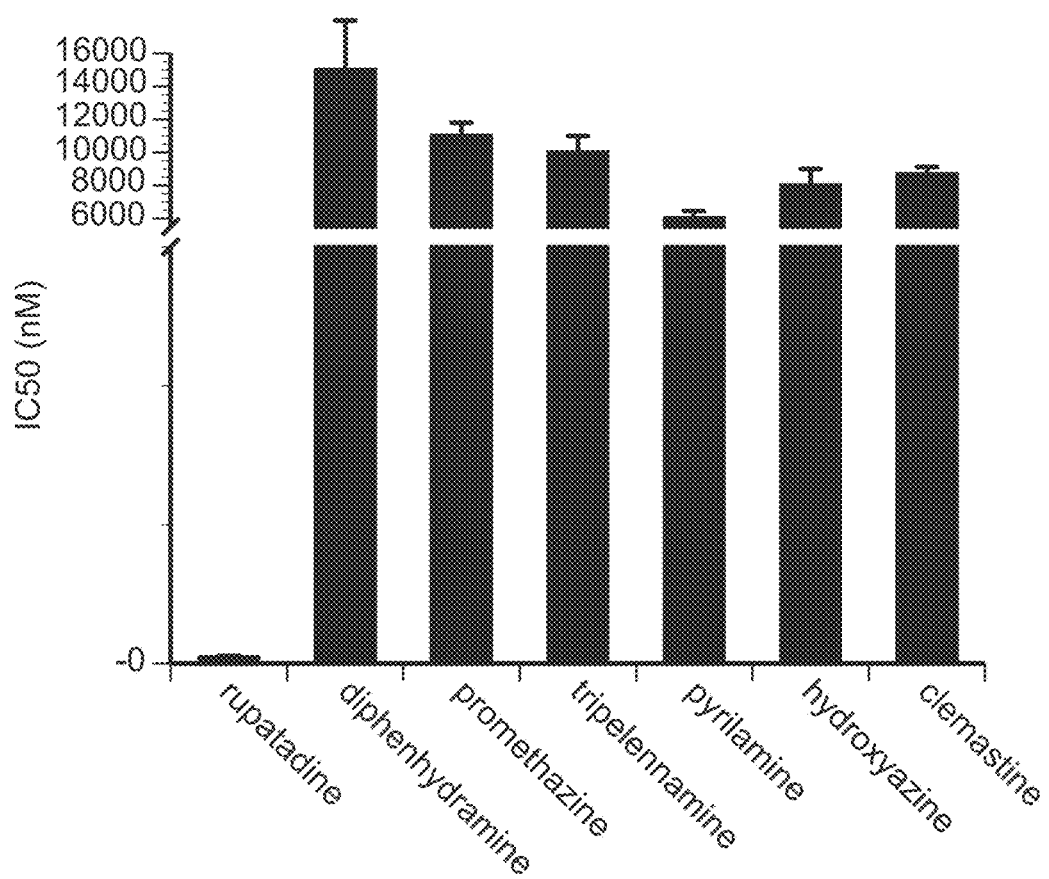
FIG. 12 shows that rupatadine blocks the bovine PAFR while other common antihistamines, diphenhydramine, promethazine, tripelennamine, pyrilamine, hydroxyazine, and clemastine, do not block the expression of PAFR.

Various antihistamines were also tested. Following transfection of the pcDNA3.3-PAFR expression vector, 10 nM PAF was added to the cells in the presence of various concentrations of the antihistamines: rupatadine, diphenhydramine, promethazine, tripelennamine, pyrilamine, hydroxyzine, or clemastine at concentrations ranging between 1-100 nM. Intracellular calcium accumulation was monitored in the transfected cells using a commercially available kit (Abcam, Cambridge). $IC_{50}$ values were then determined by identifying the concentration of the antagonist that reduced the maximal PAF-mediated intracellular calcium accumulation by 50%. As shown in FIG. 12, out of all the antihistamines, only rupatadine was able to block PAFR function.

Example 12

Figure 13:
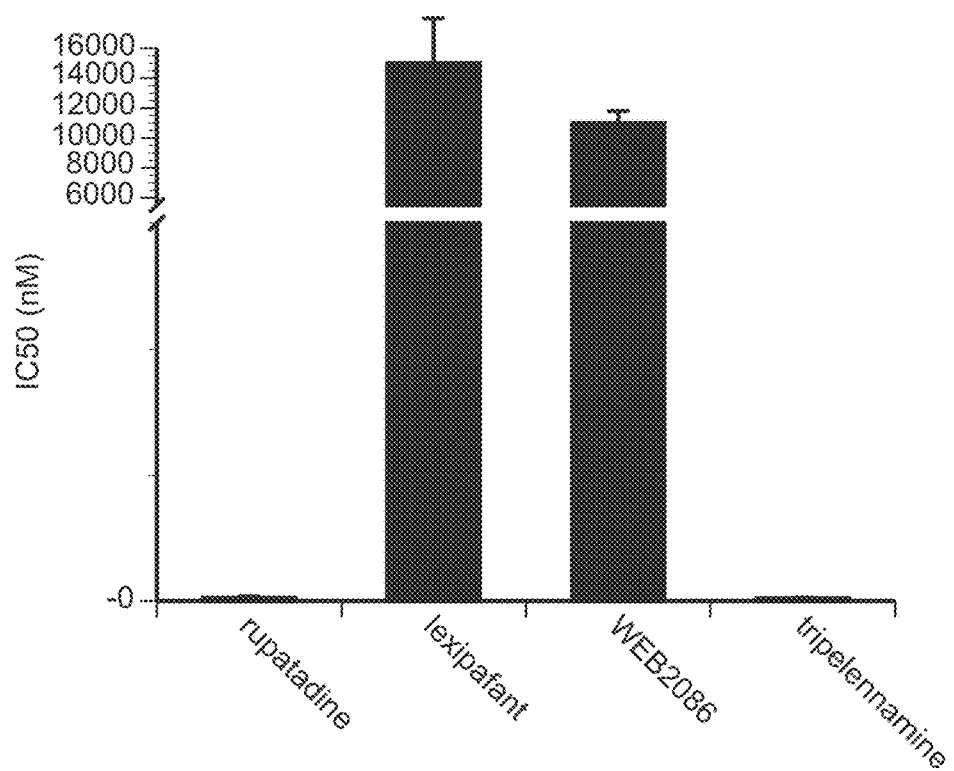
FIG. 13 shows that rupatadine and tripelennamine block the function of the H1 histamine receptor while two other PAFR antagonists, lexipafant and WEB2086, fail to black the H1 histamine receptor.

Bovine H1 histamine receptor was cloned into pcDNA3.3 expression vector and transiently expressed in BHK tissue culture cells using lipofectamine as per Carlson et al. Ten nM histamine was then added to the cells in the presence of various concentrations of rupatadine, tripelennamine, lexipafant, or WEB2086. Intracellular calcium accumulation was monitored in the transfected cells using a commercially available kit (Abcam, Cambridge, Mass.). $IC_{50}$ values were then determined by identifying the concentration of the antagonist that reduced the maximal PAF-mediated intracellular calcium accumulation by 50%. As shown in FIG. 13, rupatadine and tripelennamine were able to block the function of the H1 histamine receptor while the PAFR inhibitor did not block its function. Therefore, as showing in Examples 11 and 12, rupatadine is the only antihistamine that can also block the function of PAFR.

Example 13

Figure 14:
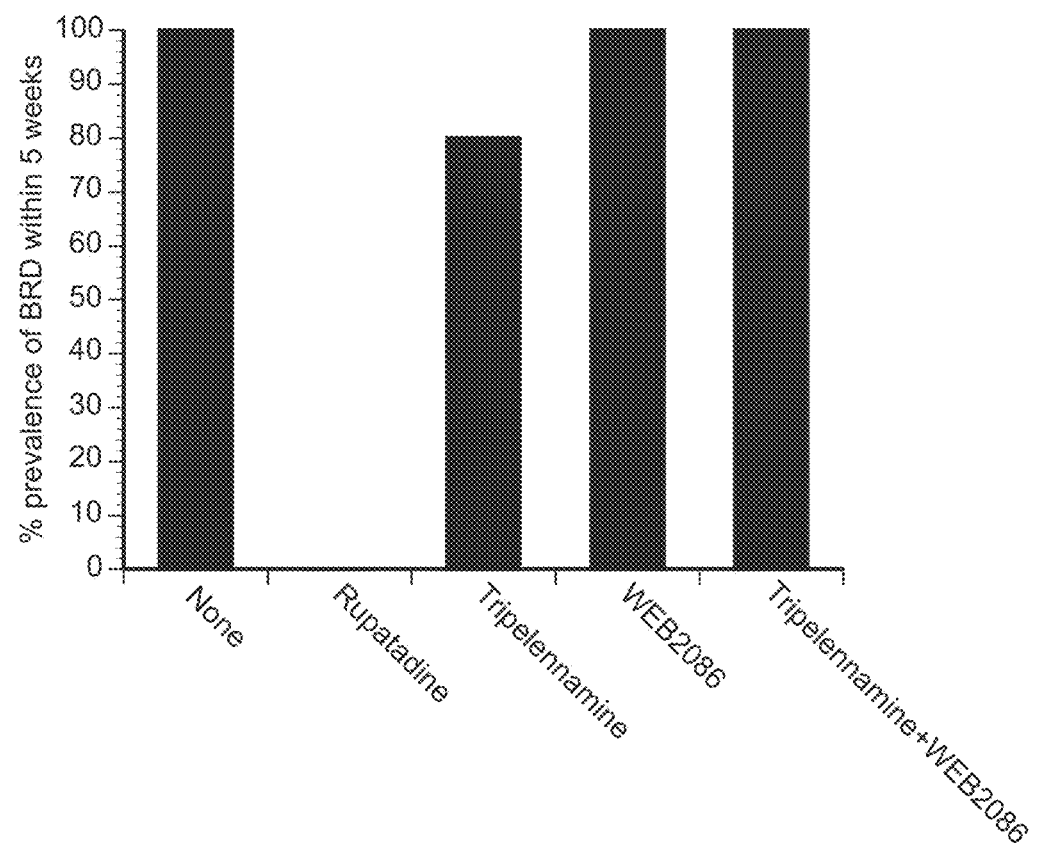
FIG. 14 shows rupatadine is more effect than other tripelennamine and WEB2086, or a combination of the two, at preventing BRD after five weeks when given as weekly injections.

Twenty-five high-risk BRD calves were transported to a new barn and five each were assigned to different treatment groups: no treatment, weekly subcutaneous injections of 7 mg/kg of rupatadine, weekly injections of 1 mg/kg tripelennamine, weekly injections of 10 mg/kg WEB2086, and weekly injections of 1 mg/kg tripelennamine and 10 mg/kg WEB2086. The animals were observed over the next five weeks twice daily for BRD. Any animal who required antibiotics for treating the clinical signs of BRD was classified as having BRD. As shown in FIG. 14, rupatadine was more effective than the other two treatments at preventing BRD. None of the five animals (0%, n=0 of 5) who received rupatadine developed BRD whereas all the control (100%, n=5 of 5), the WEB2086 (100%, n=5 of 5), and the tripelennamine plus WEB2086 (100%, n=5 of 5) treatments all resulted in contracting BRD. Four of the five (80%, n=4 of 5) animals receiving tripelennamine only developed BRD.

Figure 15:
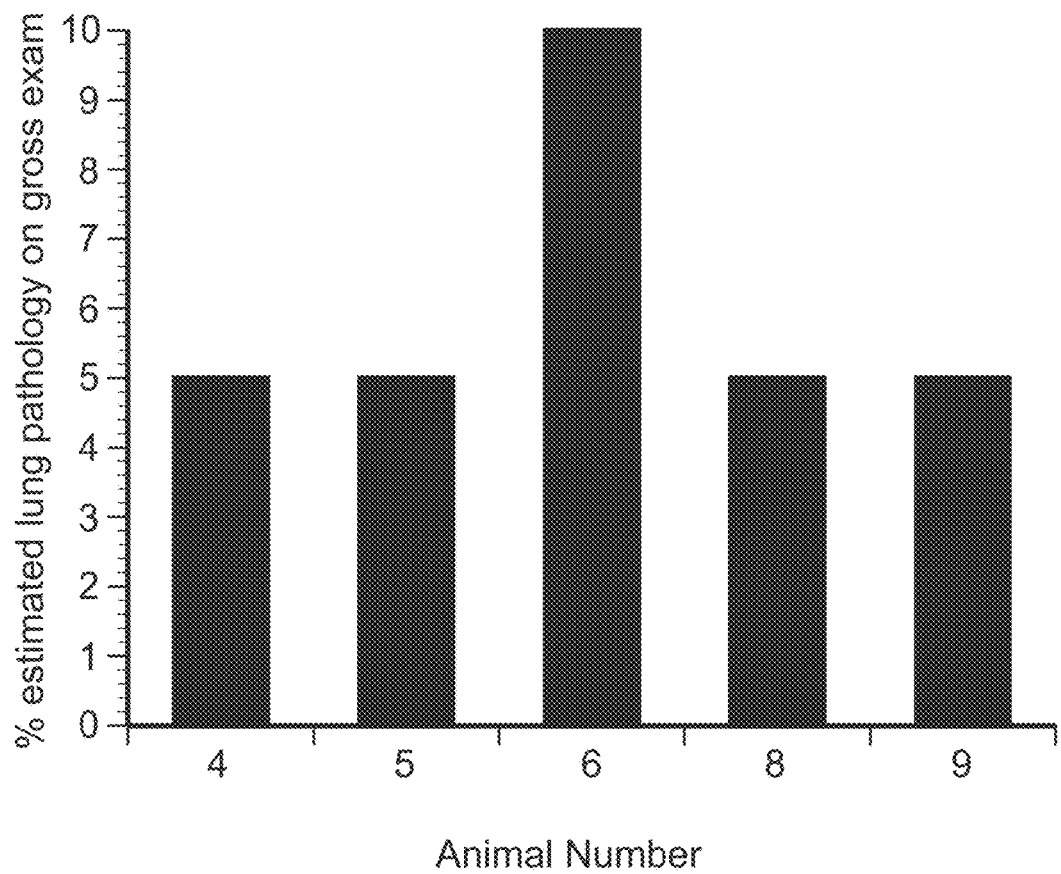
FIG. 15 shows rupatadine does not mask significant lung pathology that will hamper growth after the BRD susceptibly period ends.

After the five weeks, the rupatadine treated animals were euthanized and the lungs removed and necropsied. Three veterinarians then assessed the lungs for signs of disease, such as abscessation or consolidation. As show in FIG. 15 rupatadine does not mask significant lung pathology that will hamper growth after the BRD susceptibility period ends. Lung pathology in BRD(+) calves is usually >25%, and of the rupatadine treated animals, there was only about 5-10% disease identified by the veterinarians.

Example 14

In order to test various treatment methods of rupatadine, 25 high-risk calves were transported to a new farm. Seven calves were used as controls, six were given rupatadine as a single oral dose of 1 mg/kg, six were given rupatadine as a single subcutaneous injection of 7 mg/kg, six calves were given weekly subcutaneous injections of 7 mg/kg rupatadine. The animals were observed over the next five weeks twice daily for BRD. Any animal who required antibiotics for treating the clinical signs of BRD was classified as having BRD.

Figure 16:
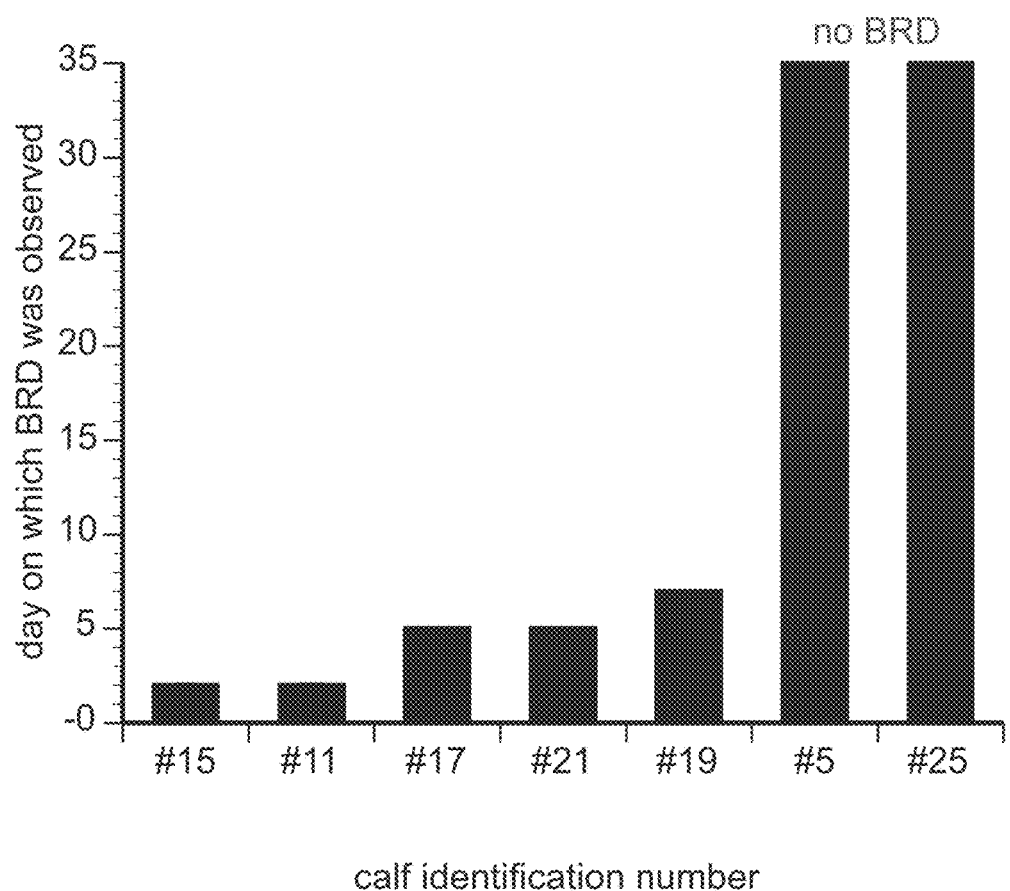
FIG. 16 shows five of seven high risk animals receiving no treatment developed BRD within the first 10 days after transportation between farms. The other two high risk animals did not develop BRD within 35 days.
Figure 17:
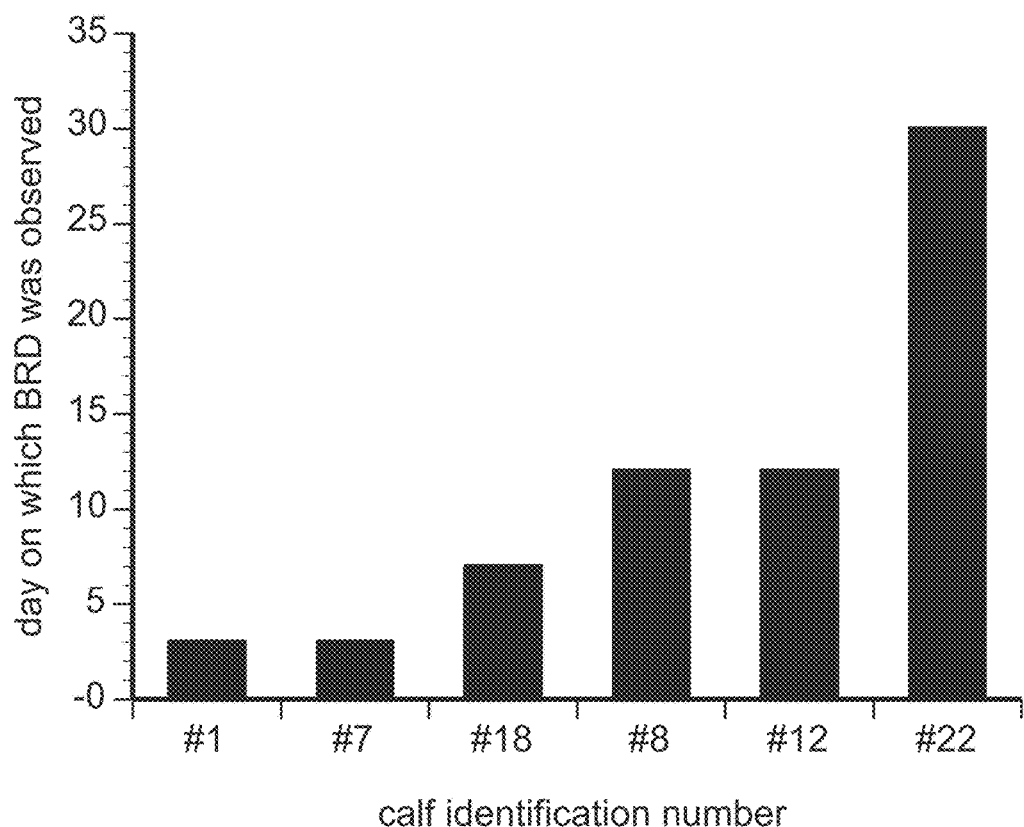
FIG. 17 shows high risk animals given a single oral dose of 1 mg/kg of rupatadine on arrival all developed BRD within 35 days after transportation between farms.
Figure 18:
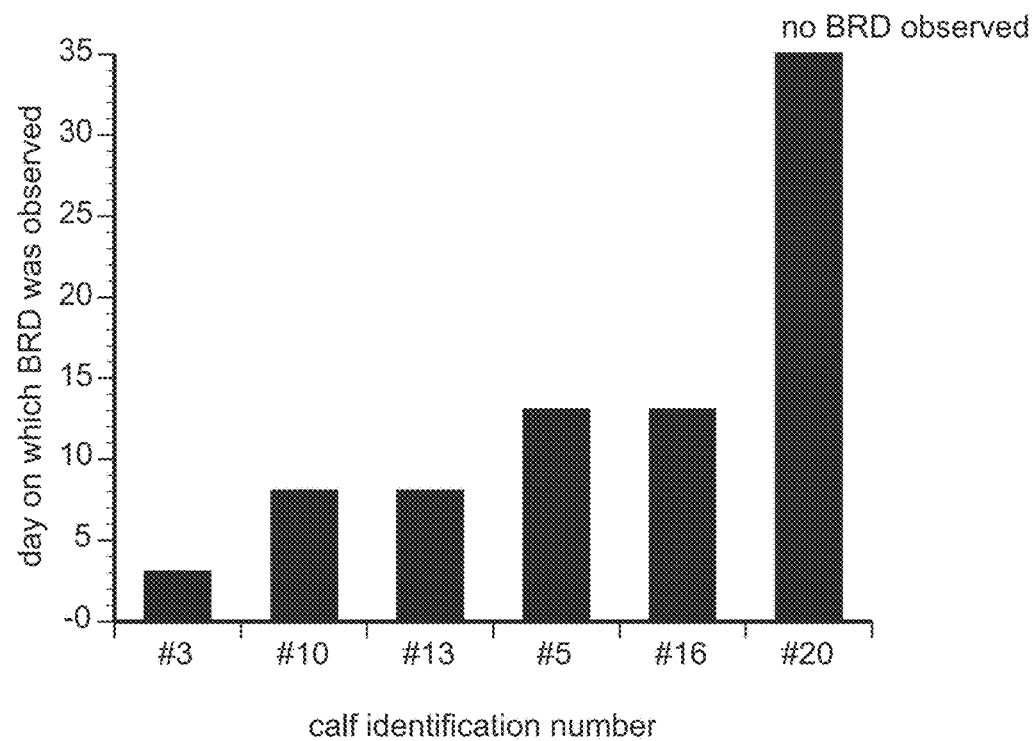
FIG. 18 shows high risk animals given a single long-acting injection of 7 mg/kg of rupatadine on arrival all developed BRD within 35 days after transportation between farms.
Figure 19:
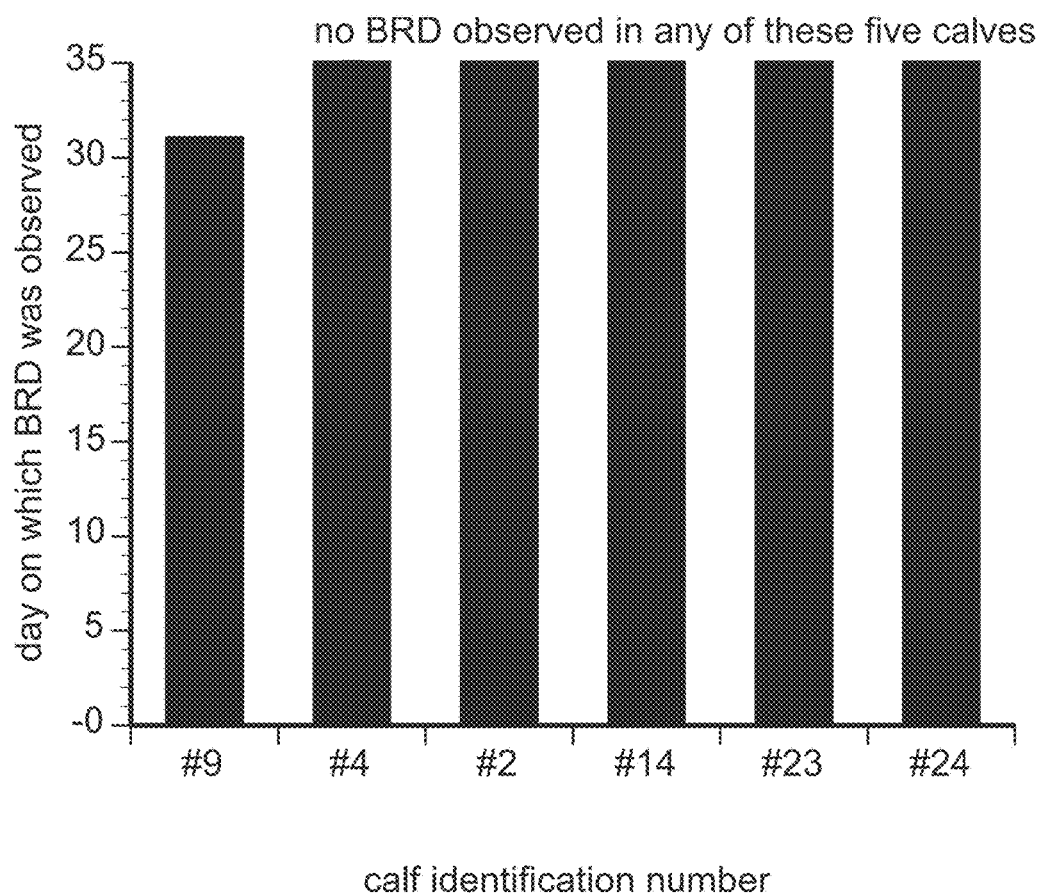
FIG. 19 shows five out of six high risk animals given weekly long-acting injections of 7 mg/kg of rupatadine did not develop BRD. The sixth animals developed BRD on day 31.
Figure 20:
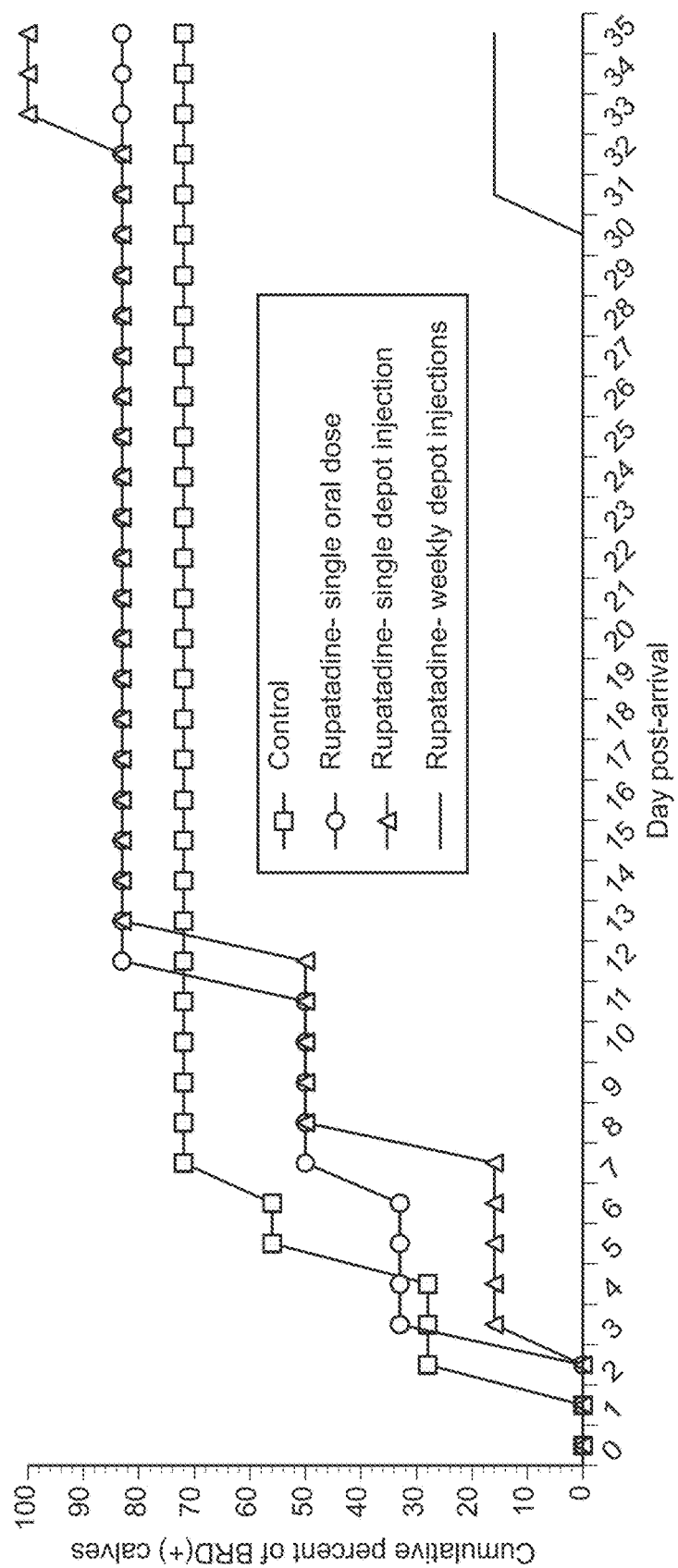
FIG. 20 show a comparison of single oral dose, single depot injection, and weekly depot injections show that the most effective treatment was the weekly depot injections.

Of the controls, as shown by FIG. 16, 28.6% (n=2 of 7) animals did not develop BRD. Of the five control calves that did, they all developed BRD between two and ten days after arrival to the new location. The single oral dose of rupatadine, as shown in FIG. 17, did not prevent BRD. All the calves (100%, n=6 of 6) eventually developed BRD between days three and 31. Similarly, as shown in FIG. 18, 83.3% (n=5 of 6) calves receiving the single, long-acting injection of rupatadine developed BRD between days three and 13. However, as shown in FIG. 19, the weekly injection of rupatadine, only 16.7% (n=1 of 6) animals developed BRD within the five-week observation. The calf that did develop BRD did so on day 31. FIG. 20 shows on which day each animal developed BRD, showing the weekly dose of rupatadine was more effective than either of the single doses.

Figure 21:
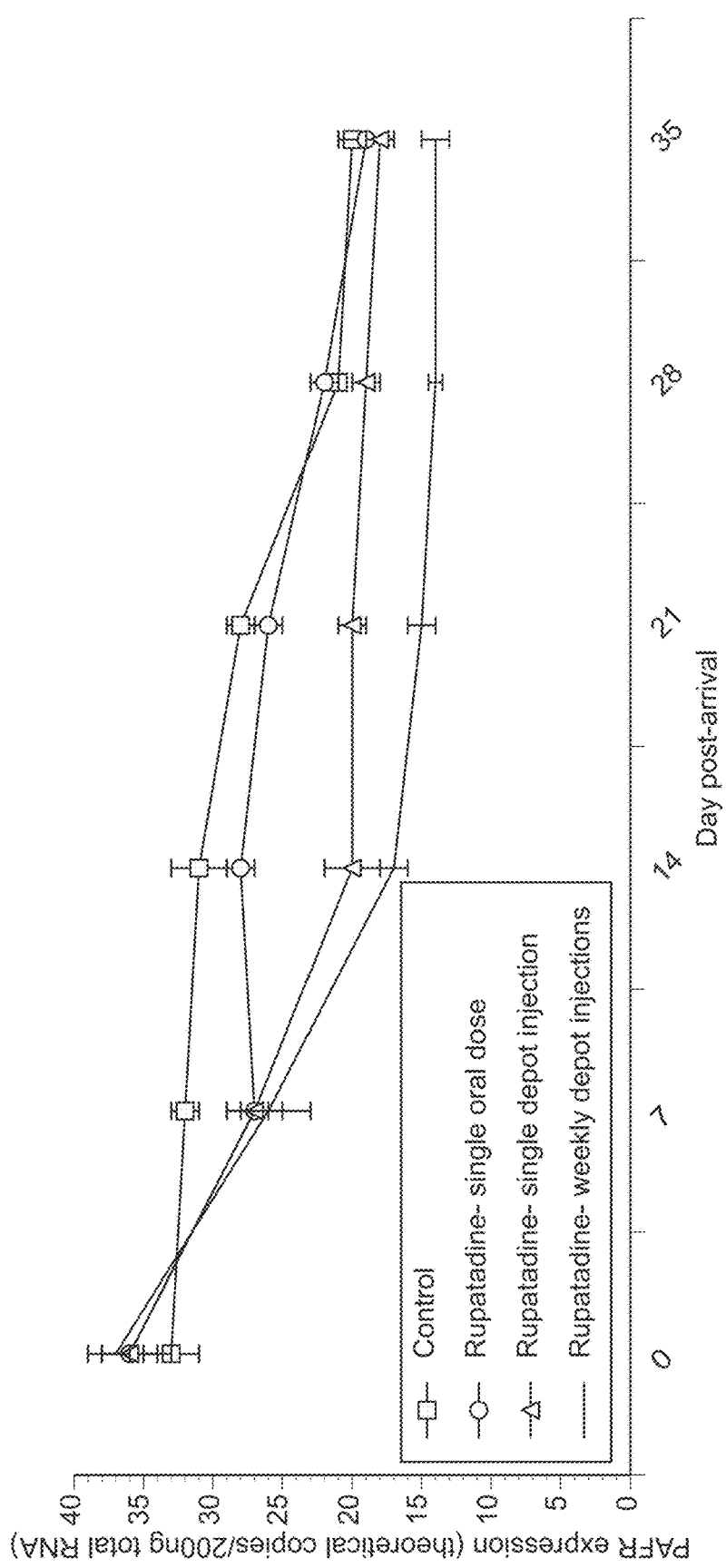
FIG. 21 shows the expression of PAFR decreases over a five-week period in control and different rupatadine treatments. Weekly depot injection of rupatadine caused the greatest decrease in PAFR expression.

Blood was extracted from all 25 calves was extracted weekly and the level of PAFR was assayed using qRT-PCR and the theoretical copies of transcript/200 ng of total RNA. As shown in FIG. 21, PAFR levels decreased over time in every experimental group. However, it dropped the most in the weekly depot injection calves during the last three weeks of observations. This data demonstrates that injections, preferably weekly injections, reduce expression of the PAFR in addition to blocking the H1 and PAFR in cattle. Beneficially, at 35 days the treated group had PAFR expression below 'normal' expression.

Example 15

Figure 22:
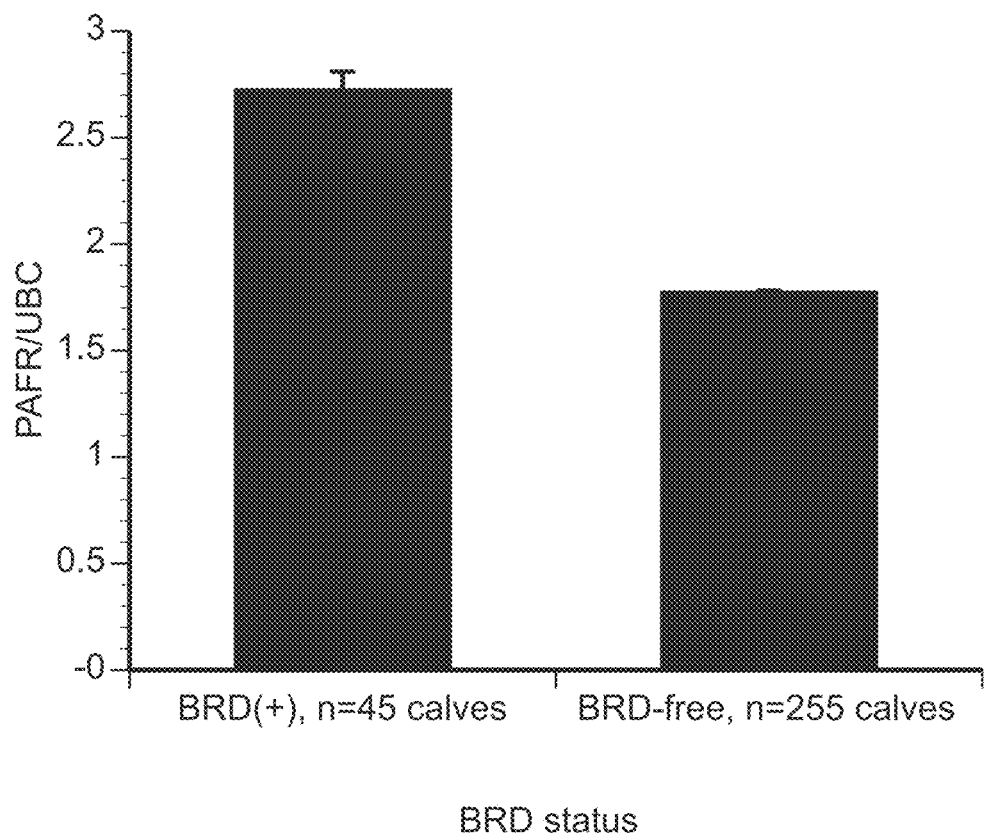
FIG. 22 shows hormone-induced PAFR expression is higher in animals that later develop BRD compared to animals who never develop BRD.

To verify the difference seen in the expression of PAFR in BRD sensitive animals to those which are not, a further study was conducted. Prior to transportation, blood was taken from 300 calves. This blood was then treated with 100 pg/mL of norepinephrine and 5 ng/mL of cortisol for 1 hour to simulate stress in order to induce expression of PLID in response to stress signals in the blood as shown in previous Examples. After 1 hour of treatment, RNA was isolated from the blood and qRT-PCR was performed on the isolated RNA. The expression of PAFR (forward primer is SEQ ID NO: 4, reverse primer is SEQ ID NO: 5) and UBC (primers purchased from QIAGEN), a house keeping gene, was assayed using qRT. The results were analyzed by calculating the theoretical copy number of each transcript/200 ng of total RNA. UBC transcript copy number was used to standardize each sample. The animals were then transported to a feedlot in another state. At the feedlot, the animals were monitored for BRD for the next six weeks. The presence or absence in this six-week period was then compared to the PAFR response seen in the pre-transportation blood samples. As shown in FIG. 22, the animals that developed BRD showed a higher, standardized, copy number of PAFR than animals who did not.

Figure 23:
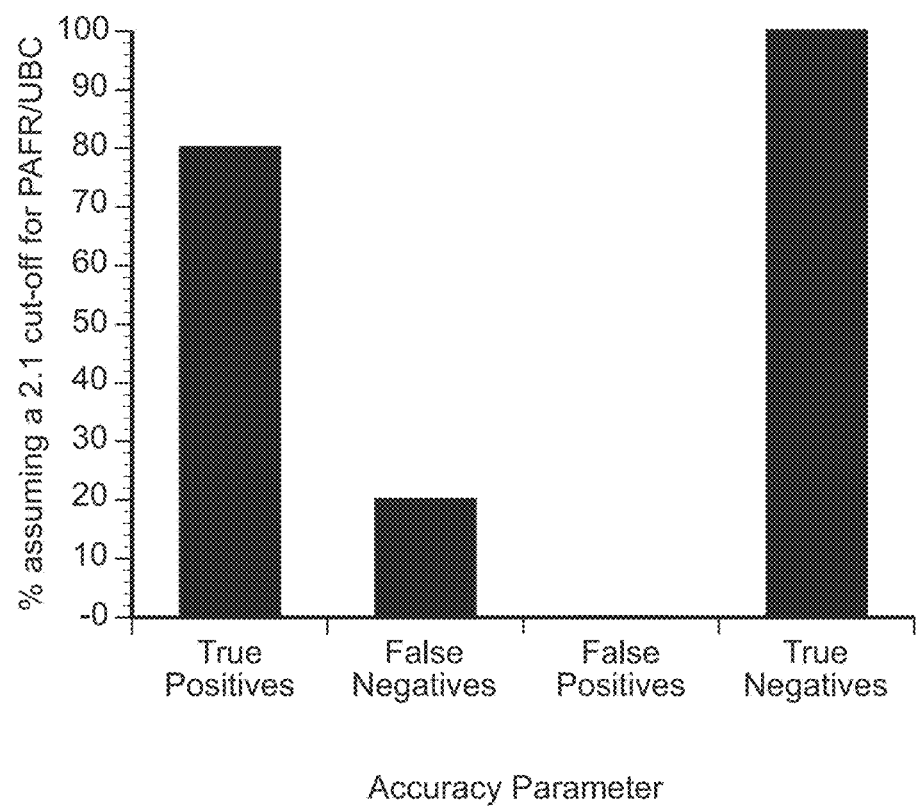
FIG. 23 shows the conservative cutoff of 2.1 PAFR/UBC RNA accurately predicts which animals will develop BRD, having a sensitivity of 80% and specificity of 100% for this dataset.

Using the same dataset, the ratio of PAFR to UBC transcript copy number was also used to determine a cutoff which may be used to predict which for animals may be BRD(+). To create a conservative predictive model, the false negative rate was minimized. A range of possible ratio cutoffs were tested in order to determine the proper cutoff value for this dataset. A cutoff ratio of 2.1 PAFR/UBC copy numbers showed no false positives (FIG. 23).

This cutoff may be used to predict how to manage animals. For instance, if the animal has not shipped to a feedlot, is tested using a stress inducing model, and shows at least about 2.1 PAFR/UBC copy number following PAFR induction, the animal may either be given prophylactic antibiotics prior to shipment or not transported to a feedlot. If an animal has already been transported, and is still stressed from the transportation, blood could be analyzed, and if found to have a ratio of about 2.1 PAFR/UBC, the animal may be given prophylactic antibiotics plus an anti-inflammatory drug.

Example 16

Particular applications of the embodiments may be supplied as kits to test for animals which may be BRD sensitive. One of skill in the art will understand from the above description, examples, and from the figures, that testing may occur at different times during the life of the animal. For example, a production manager who breeds and raises calves for finishing elsewhere may want to test the animals prior to transportation. A feedlot manager way wish to test the animals upon arrival at the feedlot or after they exhibit symptoms of BRD. Kits comprising of the various components may be assembled for each kind of situation.

By way of example, a production manager may need a more complete kit than a feedlot manager. The production manager kit may comprise of a PAFR stimulant which simulates stress and/or a compound which stimulates inflammation; an assay to measure the response of PAFR; and the instructions on how to use the kit to determine if the animal may be BRD sensitive. The PAFR stimulant may comprise of about 100 pg/mL (of sample, for instance blood) norepinephrine, about 5 ng/mL cortisol, and/or about $10^6$ CFUs/mL of lysed or inactivated bacteria. If norepinephrine and/or cortisol are used, they are added to the sample first and allowed to incubate either for about 1 hour or could be allowed to incubate overnight on ice. Following the incubation of the sample with the hormones, the lysed or inactivated bacteria may be added to the sample and allowed to incubate for about 6 hours at 37° C. The samples are then assayed for PAFR quantity. Depending on the desired target, the kit may contain reagents for assaying RNA and/or protein. If the assay is PCR based, the kit may contain the reagents to extract and quantify total RNA for PAFR and/or a housekeeping gene using techniques described herein or well known in the art. If protein level is to be quantified, the kit may contain the reagents to extract and quantify PAFR protein using techniques described herein or techniques well known in the art.

A more minimal kit may also be desired. A feedlot manager who measures the animals upon arrival may not need the PAFR stimulators of a fuller kit. A minimal kit would need to only be able to assay PAFR and contain the reagents and instruction for isolating and assaying PAFR RNA and/or protein. However, some feedlot managers may want to still use the bacterial induction following transportation, so a kit may contain the bacterial components, but not the stress simulating hormones.

It will be readily understood by those skilled in the art that specific components of the kits can be changed, and the specific ratios of specific components can also be changed within certain limits by those skilled in the art. However, it is an essential feature that the components be able to measure the expression of PAFR following stimulation.

Any of the present kits have sufficient sensitivity to provide meaningful test results, with the occurrence of false negative and false positive results being minimized. It will be readily recognized that an increase in PAFR expression as measured by the kits in response to stress and/or bacterial challenge will indicate that an animal is BRD sensitive.

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein. The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

What is claimed is:

1. A method of preventing bovine respiratory disease (BRD) in a cattle population comprising:
    administering to a population of cattle in need of BRD prevention a therapeutic anti-inflammatory agent having both anti-PAFR and anti-histamine properties comprising rupatadine or its pharmaceutically acceptable derivatives;
    wherein the therapeutic agent is administered at an amount of between about 0.1 mg/kg to about 10 mg/kg to the cattle at least once weekly and for a duration of time effective to reduce the incidence of BRD by at least 50%.

2. The method of claim 1, wherein the therapeutic agent is orally-administered.

3. The method of claim 2, wherein the therapeutic agent is provided directly to the mouth of the animal or into the feed source for the animal and the dosage form is tablets, powder, capsules, solutions (aqueous or non-aqueous), suspensions, syrups, or emulsions.

4. The method of claim 1, wherein the therapeutic agent is administered by injection.

5. The method of claim 1, wherein the therapeutic agent is dosed at an amount between about 0.3 mg/kg to about 5 mg/kg.

6. The method of claim 1, wherein the therapeutic agent is dosed once per day and administered daily for up to 28 days.

7. The method of claim 1, wherein the therapeutic agent is dosed by at least one injection and provides controlled release of the therapeutic agent.

8. The method of claim 1, wherein the method further comprises initially assaying for an increase in PAFR in a population of cattle as measured by semi-quantitative PCR, quantitative PCR, and/or protein assay, wherein semi-quantitative PCR results in a PAFR amplicon between about 7 and about 20 cycles, wherein quantitative PCR results in a PAFR/UBC ratio greater than 2, or wherein protein concentration is greater than 2 ng/mL in a protein extract.

9. The method of claim 1, wherein the incidence of BRD is reduced by at least about 50% in the population of cattle.

10. The method of claim 9, wherein the incidence of BRD is reduced by at least about 90% in the population of cattle.

11. The method of claim 9, wherein the incidence of BRD is reduced by 100% in the population of cattle.

12. The method of claim 1, wherein the therapeutic agent is administered in combination with an antibiotic.

13. The method of claim 12, wherein the antibiotic comprises Tulathromycin, Penicillin, Penicillin (Procaine/Benzathine), Oxytetracycline, Enrofloxacin, Erythromycin, Tylosin, Sulfadimethoxine, Amoxicillin, Ampicillin, Ceftoifur, Tilmicosin, Florfenicol or combinations thereof.

14. The method of claim 12, wherein the prevention of BRD results in at least a 50% reduction in antibiotic usage within a facility housing the cattle.

15. The method of claim 12, wherein the prevention of BRD results in at least a 75% reduction in antibiotic usage within a facility housing the cattle.

16. The method of claim 12, wherein the incidence of antibiotic resistance is reduced among the population of cattle.

17. The method of claim 1, wherein the therapeutic agent is absent from muscle tissues at three to six weeks post-withdrawal of the drug.

* * * * *

SEQUENCE LISTING

<160> NUMBER OF SEQ ID NOS: 5

<210> SEQ ID NO 1
<211> LENGTH: 1059
<212> TYPE: DNA
<213> ORGANISM: Bos taurus

<400> SEQUENCE: 1

```
atgaccagcc tctacttcca gcacatagag atggagccaa ataattcctt tcgtgtggac      60
tcagagttcc gatacaccct cttcccaatt ttttacagca tcgtctttgt gctgggggtc     120
```

| | |
|---|---:|
| attgccaaca gctacgtgct gtgggtcttt gcccgcttgt acccttccaa gaaattcaac | 180 |
| gagataaaga tcttcatggt gaacctcacc atggctgacc tgctcttctt ggtcaccctg | 240 |
| cccctgtgga tcgtctacta ctacaaccag ggtgactgga ttcttcccaa attcctgtgc | 300 |
| aacctggctg gctgcttctt cttcattaac acctactgct cagtggcctt cctggctgtc | 360 |
| atcacttaca accgcttcca ggcagtgaca aggcccatca agactgctca ggctaccacc | 420 |
| cgaaagcgtg gcatccttct gtccctgatt atctgggtgt ccattgtggg cgcagcatcc | 480 |
| tacttcttcg tcctggactc gaccaacagg gagcccaaca agactggctc agccaacatc | 540 |
| acacgctgct ttgaacatta cgagaagggc agcatcccgg tcctcaccat ccacatcttc | 600 |
| ctggtgttca gcttcttcct cgtcttcctc atcatcctct tttgcaactt ggtcatcatc | 660 |
| cgcacgctgc tcacgcagca ggtgcaaata cagcgcaacg ccgaggtcaa gcgccgggcg | 720 |
| ctctggatgg tctgcactgt cctggctgtg ttcatcatct gtttcgtgcc ccaccacctc | 780 |
| gtgcagctgc cctggaccct ggccgagctg gcttccagg acaccgactt ccaccaggcg | 840 |
| attaacgatg cacatcaggt cactctctgc ctccttagta ccaactgtgt cttagacccc | 900 |
| attatctact gtttcctcac caagaagttc cgcaagcacc tcaccgagaa gttgtacagt | 960 |
| atgcgcgaga gccggaagtg ctcccgggcc acctcggaga cgggcacgga agtggtcatg | 1020 |
| cagctcaaag atgtccctgt caaatccctc aaatattag | 1059 |

```
<210> SEQ ID NO 2
<211> LENGTH: 352
<212> TYPE: PRT
<213> ORGANISM: Bos taurus

<400> SEQUENCE: 2
```

Met Thr Ser Leu Tyr Phe Gln His Ile Glu Met Glu Pro Asn Asn Ser
1               5                   10                  15

Phe Arg Val Asp Ser Glu Phe Arg Tyr Thr Leu Phe Pro Ile Phe Tyr
            20                  25                  30

Ser Ile Val Phe Val Leu Gly Val Ile Ala Asn Ser Tyr Val Leu Trp
        35                  40                  45

Val Phe Ala Arg Leu Tyr Pro Ser Lys Lys Phe Asn Glu Ile Lys Ile
    50                  55                  60

Phe Met Val Asn Leu Thr Met Ala Asp Leu Leu Phe Leu Val Thr Leu
65                  70                  75                  80

Pro Leu Trp Ile Val Tyr Tyr Asn Gln Gly Asp Trp Ile Leu Pro
            85                  90                  95

Lys Phe Leu Cys Asn Leu Ala Gly Cys Phe Phe Phe Ile Asn Thr Tyr
            100                 105                 110

Cys Ser Val Ala Phe Leu Ala Val Ile Thr Tyr Asn Arg Phe Gln Ala
        115                 120                 125

Val Thr Arg Pro Ile Lys Thr Ala Gln Ala Thr Thr Arg Lys Arg Gly
    130                 135                 140

Ile Leu Leu Ser Leu Ile Ile Trp Val Ser Ile Val Gly Ala Ala Ser
145                 150                 155                 160

Tyr Phe Phe Val Leu Asp Ser Thr Asn Arg Glu Pro Asn Lys Thr Gly
            165                 170                 175

Ser Ala Asn Ile Thr Arg Cys Phe Glu His Tyr Glu Lys Gly Ser Ile
            180                 185                 190

Pro Val Leu Thr Ile His Ile Phe Leu Val Phe Ser Phe Phe Leu Val
        195                 200                 205

```
Phe Leu Ile Ile Leu Phe Cys Asn Leu Val Ile Ile Arg Thr Leu Leu
    210                 215                 220

Thr Gln Gln Val Gln Ile Gln Arg Asn Ala Glu Val Lys Arg Arg Ala
225                 230                 235                 240

Leu Trp Met Val Cys Thr Val Leu Ala Val Phe Ile Ile Cys Phe Val
                245                 250                 255

Pro His His Leu Val Gln Leu Pro Trp Thr Leu Ala Glu Leu Gly Phe
            260                 265                 270

Gln Asp Thr Asp Phe His Gln Ala Ile Asn Asp Ala His Gln Val Thr
        275                 280                 285

Leu Cys Leu Leu Ser Thr Asn Cys Val Leu Asp Pro Ile Ile Tyr Cys
    290                 295                 300

Phe Leu Thr Lys Lys Phe Arg Lys His Leu Thr Glu Lys Leu Tyr Ser
305                 310                 315                 320

Met Arg Glu Ser Arg Lys Cys Ser Arg Ala Thr Ser Glu Thr Gly Thr
                325                 330                 335

Glu Val Val Met Gln Leu Lys Asp Val Pro Val Lys Ser Leu Lys Tyr
            340                 345                 350

<210> SEQ ID NO 3
<211> LENGTH: 342
<212> TYPE: PRT
<213> ORGANISM: Homo sapiens

<400> SEQUENCE: 3

Met Glu Pro His Asp Ser Ser His Met Asp Ser Glu Phe Arg Tyr Thr
1               5                   10                  15

Leu Phe Pro Ile Val Tyr Ser Ile Ile Phe Val Leu Gly Val Ile Ala
                20                  25                  30

Asn Gly Tyr Val Leu Trp Val Phe Ala Arg Leu Tyr Pro Cys Lys Lys
            35                  40                  45

Phe Asn Glu Ile Lys Ile Phe Met Val Asn Leu Thr Met Ala Asp Met
        50                  55                  60

Leu Phe Leu Ile Thr Leu Pro Leu Trp Ile Val Tyr Tyr Gln Asn Gln
65                  70                  75                  80

Gly Asn Trp Ile Leu Pro Lys Phe Leu Cys Asn Val Ala Gly Cys Leu
                85                  90                  95

Phe Phe Ile Asn Thr Tyr Cys Ser Val Ala Phe Leu Gly Val Ile Thr
            100                 105                 110

Tyr Asn Arg Phe Gln Ala Val Thr Arg Pro Ile Lys Thr Ala Gln Ala
        115                 120                 125

Asn Thr Arg Lys Arg Gly Ile Ser Leu Ser Leu Val Ile Trp Val Ala
130                 135                 140

Ile Val Gly Ala Ala Ser Tyr Phe Leu Ile Leu Asp Ser Thr Asn Thr
145                 150                 155                 160

Val Pro Asp Ser Ala Gly Ser Gly Asn Val Thr Arg Cys Phe Glu His
                165                 170                 175

Tyr Glu Lys Gly Ser Val Pro Val Leu Ile Ile His Ile Phe Ile Val
            180                 185                 190

Phe Ser Phe Phe Leu Val Phe Leu Ile Ile Leu Phe Cys Asn Leu Val
        195                 200                 205

Ile Ile Arg Thr Leu Leu Met Gln Pro Val Gln Gln Gln Arg Asn Ala
    210                 215                 220

Glu Val Lys Arg Arg Ala Leu Trp Met Val Cys Thr Val Leu Ala Val
225                 230                 235                 240
```

```
Phe Ile Ile Cys Phe Val Pro His His Val Val Gln Leu Pro Trp Thr
            245                 250                 255

Leu Ala Glu Leu Gly Phe Gln Asp Ser Lys Phe His Gln Ala Ile Asn
            260                 265                 270

Asp Ala His Gln Val Thr Leu Cys Leu Leu Ser Thr Asn Cys Val Leu
            275                 280                 285

Asp Pro Val Ile Tyr Cys Phe Leu Thr Lys Lys Phe Arg Lys His Leu
    290                 295                 300

Thr Glu Lys Phe Tyr Ser Met Arg Ser Ser Arg Lys Cys Ser Arg Ala
305                 310                 315                 320

Thr Thr Asp Thr Val Thr Glu Val Val Val Pro Phe Asn Gln Ile Pro
                325                 330                 335

Gly Asn Ser Leu Lys Asn
            340

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
atggagccaa ataattcctt t                                              21

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ctaatatttg agggatttg                                                 19
```